US007468187B2

(12) United States Patent
Yoon et al.

(10) Patent No.: US 7,468,187 B2
(45) Date of Patent: Dec. 23, 2008

(54) CANINE INFLUENZA VIRUS AND RELATED COMPOSITIONS AND METHODS OF USE

(75) Inventors: Kyoung-Jin Yoon, Ames, IA (US); Vickie Cooper, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 11/539,123

(22) Filed: Oct. 5, 2006

(65) Prior Publication Data

US 2007/0098742 A1 May 3, 2007

Related U.S. Application Data

(60) Provisional application No. 60/727,808, filed on Oct. 18, 2005.

(51) Int. Cl.
*A61K 39/145* (2006.01)
*A61K 39/00* (2006.01)
*A61K 39/12* (2006.01)
*A61K 39/02* (2006.01)

(52) U.S. Cl. .............. 424/209.1; 424/185.1; 424/186.1; 424/204.1

(58) Field of Classification Search ...................... None
See application file for complete search history.

(56) References Cited

U.S. PATENT DOCUMENTS

| | | | |
|---|---|---|---|
| 3,991,179 | A | 11/1976 | Beare et al. |
| 4,009,258 | A | 2/1977 | Kilbourne |
| 4,029,763 | A | 6/1977 | Kilbourne |
| 4,140,762 | A | 2/1979 | Bachmayer et al. |
| 4,278,662 | A | 7/1981 | Löbmann et al. |
| 4,318,903 | A | 3/1982 | Löbmann et al. |
| 4,338,296 | A | 7/1982 | Löbmann et al. |
| 4,693,893 | A | 9/1987 | Campbell |
| 4,826,687 | A | 5/1989 | Nerome et al. |
| 5,136,019 | A | 8/1992 | Judd et al. |
| 5,162,112 | A | 11/1992 | Oxford et al. |
| 5,616,327 | A | 4/1997 | Judd et al. |
| 5,741,493 | A | 4/1998 | Moste-Deshairs et al. |
| 5,762,939 | A | 6/1998 | Smith et al. |
| 6,245,532 | B1 | 6/2001 | Smith et al. |
| 6,605,457 | B1 | 8/2003 | Fiers et al. |
| 6,740,325 | B1 | 5/2004 | Arnon et al. |
| 2003/0129197 | A1 | 7/2003 | Fiers et al. |
| 2003/0199074 | A1 | 10/2003 | Dowling et al. |
| 2007/0082012 | A1* | 4/2007 | Shields et al. ............. 424/209.1 |

FOREIGN PATENT DOCUMENTS

| | | |
|---|---|---|
| WO | WO 00/09702 | 8/2000 |
| WO | WO 01/60849 | 2/2001 |

OTHER PUBLICATIONS

Anderson et al., "Canine Influenza Virus Agglutination of Avian and Mammalian Red Blood Cells," *Proceedings of the American Association of Veterinary Laboratory Diagnosticians 49th Annual Conference*, p. 44 (2006).
Anderson et al., "Development of a Hemagglutination Inhibition Assay for Diagnosis of Canine Influenza Virus Infection," *Proceedings of the American Association of Veterinary Laboratory Diagnosticians 49th Annual Conference*, p. 45 (2006).
Crawford et al., "Transmission of Equine Influenza Virus to Dogs," *Science*, 310: pp. 482-485 (2005).
Daly, "Equine Influenza in dogs: Too late to bolt the stable door?," *The Veterinary Journal*, 171 pp. 7-8 (2006).
Dubovi et al., "Isolation of Equine Influenza Virus from Racing Greyhounds with Fatal Hemorrhagic Pneumonia," In: *Proceedings of the 47th Annual Meeting of American Association of Veterinary Laboratory Diagnosticians*, Greensboro, NC, p. 158 (2005).
Joly, "Canine Influenza Virus" *The Veterinary Record*, p. 527 (2005).
Keawcharoen et al., "Avian Influenza H5N1 in Tigers and Leopards," *Emerg. Infect. Dis.*, 10: pp. 2189-2191 (2004).
Macken et al., "The value of a database in surveillance and vaccine selection," In: *Options for the Control of Influenza IV*, Osterhaus et al., eds. Elsevier Science, Amsterdam, pp. 103-106 (2001).
Smith et al., "Canine Influenza Virus" *The Veterinary Record*, p. 599 (2005).
Yoon et al., "Influenza Virus Infection in Racng Greyhounds," *Emerg. Infect. Dis.*, 11(12): pp. 1974-1976 (2005).
Crawford et al.: "Influenza A virus (A/canine/Texas/1/2004 (H3N9))" Database accession No. DQ124159 (2005).
Quinlivan et al., "Attenuation of equine influenza viruses through truncations of the N protein," Database accession No. Q5BUA9 (2005).
Quinlivan et al., "Attenuation of equine influenza viruses through truncations of the N protein," Database accession No. Q5BUA7 (2005).
Quinlivan et al.; "Attenuation of equine influenza viruses through truncations of the N protein," Database accession No. Q5BUB2 (2005).
Quinlivan et al.: "Attenuation of equine influenza viruses through truncations of the N protein," Database accession No. Q5BUB3 (2005).
Lindstrom et al.: "Phylogenetic analyses of the matrix and non-structural genes of equine influenza virusesr," Archives of Virology, New York, vol. 143, No. 8, 1998, pp. 1585-1598, NY, US, ISSN: 0304-8608, the whole document (1998).

(Continued)

*Primary Examiner*—Bruce Campell
*Assistant Examiner*—Benjamin P Blumel
(74) *Attorney, Agent, or Firm*—Barnes & Thornburg LLP; Sendil K. Devadas

(57) ABSTRACT

The present invention provides an isolated canine influenza virus of subtype H3N8 comprising an HA having SEQ ID NO: 4 or an amino acid sequence that is greater than 99% identical to SEQ ID NO: 4 , with the proviso that the amino acids at positions 94 and 233 are identical to SEQ ID NO: 4; a composition comprising attenuated or inactivated virus; isolated or purified HA, NM, NP, M1 , NS1 , PA, PB1 , and PB2 proteins and fragments thereof and compositions comprising same or nucleic acids, optionally as part of a vector, encoding same; and a method of inducing an immune response to canine influenza virus in an animal comprising administering to the animal an aforementioned composition.

6 Claims, 14 Drawing Sheets

OTHER PUBLICATIONS

Ito, T. et al.: "Evolutionary analysis of the influenza a virus M gene with comparison of the M1 and M2 proteins," Journal of Virology, vol. 65, No. 10, 1991, pp. 5491-5498, ISSN: 0022-538X, 06173, the whole document (1991).
Peek, Simon F. et al: "Acute respiratory distress syndrome and fatal interstitial pneumonia associated with equine influenza in a neonatal foal," Journal of Veterinary Internal Medicine, Lippincott, Philidelphia, U.S., vol. 18, No. 1, pp. 132-134 (2004).
Peek et al.: Database accession No. Q30BG0 (2005).
Peek et al.: Database accession No. Q30BG2 (2005).
Peek et al.: Database accession No. Q30BG4 (2005).
Peek et al.: Database accession No. Q30BG5 (2005).
Peek et al.: Database accession No. Q30BG6 (2005).
Peek et al.: Database accession No. Q30BF7 (2005).
Peek et al.: Database accession No. Q30BF8 (2005).
Peek et al.: Database accession No. Q30BF9 (2005).
Yoon, K. -L. et al.: "Influenza virus A (A/canine/Iowa/13628/2005 (H3N8))," Database accession No. Q2XXL0 (2005).
Int'l Search Report issued in corresponding application No. PCT/US06/060025 (2007).

* cited by examiner

NM
AGTTTAAAATGAATCCAAATCAAAAGATAATAGCAATTGGATTTGCATCATTGGG
GATATTAATCATTAATGTCATTCTCCATGTAGTCAGCATTATAGTAACAGTACTG
GTCCTCAATAACAATAGAACAGATCTGAACTGCAAAGGGACGATCATAAGAGAA
TACAATGAAACAGTAAGAGTAGAAAAACTTACTCAATGGTATAATACCAGTACA
ATTAAGTACATAGAGAGACCTTCAAATGAATACTACATGAATAACACTGAACCA
CTTTGTGAGGCCCAAGGCTTTGCACCATTTTCCAAAGATAATGGAATACGAATTG
GGTCGAGAGGCCATGTTTTTGTGATAAGAGAACCTTTTGTATCATGTTCGCCCTC
AGAATGTAGAACCTTTTTCCTCACACAGGGCTCATTACTCAATGACAAACATTCT
AACGGCACAATAAAGGATCGAAGCCCGTATAGGACTTTGATGAGTGTCAAAATA
GGGCAATCACCCAATGTATATCAAGCTAGGTTTGAATCGGTGGCATGGTCAGCA
ACAGCATGCCATGATGGAAAAAATGGATGACAGTTGGAGTCACAGGGCCCGAC
AATCAAGCAATTGCAGTAGTGAACTATGGAGGTGTTCCGGTTGATACTATTAATT
CATGGGCAGGGGATATTTTAAGAACCCAAGAATCATCATGCACCTGCATTAAAG
GAGACTGTTATTGGGTAATGACTGATGGACCGGCAAATAGGCAAGCTAAATATA
GGATATTCAAAGCAAAGATGGAAGAGTAATTGGACAAACTGATATAAGTTTCA
ATGGGGGACACATAGAGGAGTGTTCTTGTTACCCCAATGAAGGGAAGGTGGAAT
GCATATGCAGGGACAATTGGACTGGAACAAATAGACCAATTCTGGTAATATCTTC
TGATCTATCGTACACAGTTGGATATTTGTGTGCTGGCATTCCCACTGACACTCCTA
GGGGAGAGGATAGTCAATTCACAGGCTCATGTACAAGTCCTTTGGGAAATAAAG
GATACGGTGTAAAAGGCTTCGGGTTTCGACAAGGAACTGACGTATGGGCCGGAA
GGACAATTAGTAGGACTTCAAGATCAGGATTCGAAATAATAAAAATCAGGAATG
GTTGGACACAGAACAGTAAGGACCAAATCAGGAGGCAAGTGATTATCGATGACC
CAAATTGGTCAGGATATAGCGGTTCTTTCACATTGCCGGTTGAACTGACAAAAAA
GGGATGTTTGGTCCCCTGTTTCTGGGTTGAAATGATTAGAGGTAAACCTGAAGAA
ACAACAATATGGACCTCTAGCAGCTCCATTGTGATGTGTGGAGTAGATCATAAAA
TTGCCAGTTGGTCATGGCACGATGGAGCTATTCTTCCCTTTGACATCGATAAGAT
GTAATTTACGAAAAAACTCCTTGTTTCTACTA (SEQ ID NO: 1)

FIG. 1

NM - Amino

MNPNQKIIAIGFASLGILIINVILHVVSIIVTVLVLNNNRTDLNCKGTIIREYNETVRVEK
LTQWYNTSTIKYIERPSNEYYMNNTEPLCEAQGFAPFSKDNGIRIGSRGHVFVIREPFV
SCSPSECRTFFLTQGSLLNDKHSNGTIKDRSPYRTLMSVKIGQSPNVYQARFESVAWS
ATACHDGKKWMTVGVTGPDNQAIAVVNYGGVPVDTINSWAGDILRTQESSCTCIKG
DCYWVMTDGPANRQAKYRIFKAKDGRVIGQTDISFNGGHIEECSCYPNEGKVECICR
DNWTGTNRPILVISSDLSYTVGYLCAGIPTDTPRGEDSQFTGSCTSPLGNKGYGVKGF
GFRQGTDVWAGRTISRTSRSGFEIIKIRNGWTQNSKDQIRRQVIIDDPNWSGYSGSFTL
PVELTKKGCLVPCFWVEMIRGKPEETTIWTSSSSIVMCGVDHKIASWSWHDGAILPF
DIDKM (SEQ ID NO: 2)

AGCAAAAGCAGGGGATATTTCTGTCAATCATGAAGACAACCATTATTTTAATACT
ACTGACCCATTGGGCCTACAGTCAAAACCCAATCAGTGGCAATAACACAGCCAC
ACTGTGTCTGGGACACCATGCAGTAGCAAATGGAACATTGGTAAAAACAATGAG
TGATGATCAAATTGAGGTGACAAATGCTACAGAATTAGTTCAGAGCATTTCAATG
GGGAAAATATGCAACAAATCATATAGAATTCTAGATGGAAGAAATTGCACATTA
ATAGATGCAATGCTAGGAGACCCCCACTGTGACGCCCTTCAGTATGAGAGTTGG
GACCTCTTTATAGAAAGAAGCAGCGCTTTCAGCAATTGCTACCCATATGACATCC
CTGACTATGCATCGCTCCGATCCATTGTAGCATCCTCAGGAACAGTTGAATTCAC
AGCAGAGGGATTCACATGGACAGGTGTAACTCAAAACGGAAGAAGTGGAGCCTG
CaaAAGGGGATCAGCCGATAGTTTCTTTAGCCGACTGAATTGGCTAACAAAATCT
GGAAGCTCTTACCCCACATTGAATGTGACAATGCCTAACAATAAAAATTTCGACA
AGCTATACATCTGGGGGATTCATCACCCGAGCTCAAATCAAGAGCAGACAAAAT
TGTACATCCAAGAATCAGGACGAGTAACAGTCTCAACAAAAAGAAGTCAACAAA
CAATAATCCCTAACATCGAATCTAGACCGTTGGTCAGAGGTCAATCAGGCAGGA
TAAGCATATACTGGACCATTGTAAAACCTGGAGATATCCTAATGATAAACAGTA
ATGGCAACTTAGTTGCACCGCGGGGATATTTTAAATTGAACACAGGGAAAAGCT
CTGTAATGAGATCCGATGTACCCATAGACATTTGTGTGTCTGAATGTATTACACC
AAATGGAAGCATCTCCAACGACAAGCCATTCCAAAATGTGAACAAAGTTACATA
TGGAAAATGCCCCAAGTATATCAGGCAAAACACTTTAAAGCTGGCCACTGGGAT
GAGGAATGTACCAGAAAAGCAAACCAGAGGAATCTTTGGAGCAATAGCGGGATT
CATCGAAAACGGCTGGGAAGGAATGGTTGATGGGTGGTATGGGTTCCGATATCA
AAACTCTGAAGGAACAGGGCAAGCTGCAGATCTAAAGAGCACTCAAGCAGCCAT
TGACCAGATTAATGGAAAGTTAAACAGAGTGATTGAAAGAACCAATGAGAAATT
CCATCAAATAGAGAAGGAATTCTCAGAAGTAGAAGGAAGAATTCAGGACTTGGA
GAAATATGTAGAAGACACCAAAATAGACCTATGGTCCTACAATGCAGAATTGCT
GGTGGCTCTAGAAAATCAACATACAATTGACTTAACAGATGCAGAAATGAATAA
ATTATTTGAGAAGACTAGACGCCAGTTAAGAGAAAACGCAGAAGACATGGGAGG
TGGATGTTTCAAGATTTACCACAAATGTGATAATGCATGCATTGAATCAATAAGA
ACTGGGACATATGACCATTACATATACAGAGATGAAGCATTAAACAACCGATTT
CAGATCAAAGGTGTAGAGTTGAAATCAGGCTACAAAGATTGGATACTGTGGATT
TCATTCGCCATATCATGCTTCTTAATTTGCGTTGTTCTATTGGGTTTCATTATGTGG
GCTTGCCAAAAAGGCAACATCAGATGCAACATTTGCATTTGAGTAAACTGATAGT
TAAAAACACCCTTGTTTCTACT (SEQ ID NO:3)

FIG. 3

HA - Amino

MKTTIILILLTHWAYSQNPISGNNTATLCLGHHAVANGTLVKTMSDDQIEVTNATEL
VQSISMGKICNKSYRILDGRNCTLIDAMLGDPHCDALQYESWDLFIERSSAFSNCYPY
DIPDYASLRSIVASSGTVEFTAEGFTWTGVTQNGRSGACKRGSADSFFSRLNWLTKS
GSSYPTLNVTMPNNKNFDKLYIWGIHHPSSNQEQTKLYIQESGRVTVSTKRSQQTIIP
NIESRPLVRGQSGRISIYWTIVKPGDILMINSNGNLVAPRGYFKLNTGKSSVMRSDVPI
DICVSECITPNGSISNDKPFQNVNKVTYGKCPKYIRQNTLKLATGMRNVPEKQTRGIF
GAIAGFIENGWEGMVDGWYGFRYQNSEGTGQAADLKSTQAAIDQINGKLNRVIERT
NEKFHQIEKEFSEVEGRIQDLEKYVEDTKIDLWSYNAELLVALENQHTIDLTDAEMN
KLFEKTRRQLRENAEDMGGGCFKIYHKCDNACIESIRTGTYDHYIYRDEALNNRFQI
KGVELKSGYKDWILWISFAISCFLICVVLLGFIMWACQKGNIRCNICI (SEQ ID NO: 4)

CAGGGAGCAAAAGCAGGGTAGATAATCACTCACTGAGTGACATCAAAGTCATGG
CGTCTCAAGGCACCAAACGATCCTATGAACAGATGGAAACTGATGGGGAACGCC
AGAATGCAACTGAAATCAGAGCATCTGTCGGAAGGATGGTGGGAGGAATCGGAC
GGTTTTATGTCCAGATGTGTACTGAGCTTAAACTAAACGACCATGAAGGGCGGCT
GATTCAGAACAGCATAACAATAGAAGGATGGTACTTTCAGCATTCGACGAAAG
AAGAAACAAGTATCTCGAGGAGCATCCCAGTGCTGGGAAAGACCCTAAGAAAAC
GGGAGGCCCGATATACAGAAGAAAGATGGGAAATGGATGAGGGAACTCATCC
TCCATGATAAAGAAGAAATCATGAGAATCTGGCGTCAGGCCAACAATGGTGAAG
ACGCTACTGCTGGTCTTACTCATATGATGATCTGGCACTCCAATCTCAATGACAC
CACATACCAAAGAACAAGGGCTCTTGTTCGGACTGGGATGGATCCCAGAATGTG
CTCTCTGATGCAAGGCTCAACCCTCCCACGGAGATCTGGAGCCGCTGGTGCTGCA
GTAAAAGGTGTTGGAACAATGGTAATGGAACTCATCAGGATGATCAAACGCGGA
ATAAATGATCGGAATTTCTGGAGAGGTGAAAATGGTCGAAGAACCAGAATTGCT
TATGAAAGAATGTGCAATATCCTCAAAGGGAAATTTCAGACAGCAGCACAACGG
GCTATGATGGACCAGGTGAGGGAAGGCCGCAATCCTGGAAACGCTGAGATTGAG
GATCTCATTTTCTTGGCACGATCAGCACTTATTTTGAGAGGATCAGTAGCCCATA
AATCATGCCTACCTGCCTGTGTTTATGGCCTTGCAGTAACCAGTGGGTATGACTTT
GAGAAGGAAGGATACTCTCTGGTTGGAATTGATCCTTTCAAACTACTCCAGAACA
GTCAAATTTTCAGTCTAATCAGACCAAAAGAAAACCCAGCACACAAAAGCCAGT
TGGTGTGGATGGCATGCCATTCTGCAGCATTTGAGGATCTGAGAGTTTTAAATTT
CATTAGAGGAACCAAAGTAATCCCAAGAGGACAGTTAACAACCAGAGGAGTTCA
AATTGCTTCAAATGAAAACATGGAGACAATAAATTCTAGCACACTTGAACTGAG
AAGCAAATATTGGGCAATAAGGACCAGAAGCGGAGGAAACACCAGTCAACAGA
GAGCATTTGCAGGACAGATAAGTGTGCAACCTACTTTCTCAGTACAGAGAAATCT
TCCCTTTGAGAGAGCAACCATTATGGCTGCATTCACTGGTAACACTGAAGGGAGG
ACTTCCGACATGAGAACGGAAATCATAAGGATGATGGAAAATGCCAAATCAGAA
GATGTGTCTTTCCAGGGGCGGGGAGTCTTCGAGCTCTCGGACGAAAAGGCAACG
AACCCGATCGTGCCTTCCTTTGACATGAGCAATGAAGGGTCTTATTTCTTCGGAG
ACAATGCTGAGGAGTTTGACAGTTAAAGAAAAATACCCTTGTTTCTACTAATACG
AGACGATAT (SEQ ID NO: 5)

FIG. 5

NP - Amino

MASQGTKRSYEQMETDGERQNATEIRASVGRMVGGIGRFYVQMCTELKLNDHEGR
LIQNSITIERMVLSAFDERRNKYLEEHPSAGKDPKKTGGPIYRRKDGKWMRELILHD
KEEIMRIWRQANNGEDATAGLTHMMIWHSNLNDTTYQRTRALVRTGMDPRMCSL
MQGSTLPRRSGAAGAAVKGVGTMVMELIRMIKRGINDRNFWRGENGRRTRIAYER
MCNILKGKFQTAAQRAMMDQVREGRNPGNAEIEDLIFLARSALILRGSVAHKSCLPA
CVYGLAVTSGYDFEKEGYSLVGIDPFKLLQNSQIFSLIRPKENPAHKSQLVWMACHS
AAFEDLRVLNFIRGTKVIPRGQLTTRGVQIASNENMETINSSTLELRSKYWAIRTRSG
GNTSQQRAFAGQISVQPTFSVQRNLPFERATIMAAFTGNTEGRTSDMRTEIIRMMEN
AKSEDVSFQGRGVFELSDEKATNPIVPSFDMSNEGSYFFGDNAEEFDS (SEQ ID NO: 6)

TATTCGTCTCAGGGAGCAAAAGCAGGTAGATATTTAAAGATGAGTCTTCTAACCG
AGGTCGAAACGTACGTTCTCTCTATCGTACCATCAGGCCCCCTCAAAGCCGAGAT
CGCGCAGAGACTTGAAGATGTCTTTGCGGGAAAGAACACCGATCTTGAGGCACT
CATGGAATGGCTAAAGACAAGACCAATCCTGTCACCTCTGACTAAAGGGATTTTA
GGATTTGTATTCACGCTCACCGTGCCCAGTGAGCGAGGACTGCAGCGTAGACGCT
TTGTCCAAAATGCCCTTAGTGGAAACGGAGATCCAAACAACATGGACAGAGCAG
TAAAACTGTACAGGAAGCTTAAAAGAGAAATAACATTCCATGAGGCAAAAGAGG
TGGCACTCAGCTATTCCACTGGTGCACTAGCCAGCTGCATGGGACTCATATACAA
CAGAATGGGAACTGTTACAACCGAAGTGGCATTTGGCCTGGTATGCGCCACATGT
GAACAGATTGCTGATTCCCAGCATCGATCTCACAGGCAGATGGTGACAACAACC
AACCCATTAATCAGACATGAAAACAGAATGGTATTAGCCAGTACCACGGCTAAA
GCCATGGAACAGATGGCAGGATCGAGTGAGCAGGCAGCAGAGGCCATGGAGGT
TGCTAGTAGGGCTAGGCAGATGGTACAGGCAATGAGAACCATTGGGACCCACCC
TAGCTCCAGTGCCGGTTTGAAAGATGATCTCCTTGAAAATTTACAGGCCTACCAG
AAACGGATGGGAGTGCAAATGCAGCGATTCAAGTGATCCTCTCGTTATTGCAGC
AAGTATCATTGGAATCTTGCACTTGATATTGTGGATTCTTGATCGTCTTTTCTTCA
AATTCATTTATCGTCGCCTTAAATACGGGTTGAAAAGAGGGCCTTCTACGGAAGG
AGTACCTGAGTCTATGAGGGAAGAATATCGGCAGGAACAGCAGAATGCTGTGGA
TGTTGACGATGGTCATTTTGTCAACATAGAGCTGGAGTAAAAAACTACCTTGTTT
CTACTAATACGAGACGATAT (SEQ ID NO: 7)

FIG. 7

M1 - Amino

MSLLTEVETYVLSIVPSGPLKAEIAQRLEDVFAGKNTDLEALMEWLKTRPILSPLTKG
ILGFVFTLTVPSERGLQRRRFVQNALSGNGDPNNMDRAVKLYRKLKREITFHEAKEV
ALSYSTGALASCMGLIYNRMGTVTTEVAFGLVCATCEQIADSQHRSHRQMVTTTNP
LIRHENRMVLASTTAKAMEQMAGSSEQAAEAMEVASRARQMVQAMRTIGTHPSSS
AGLKDDLLENLQAYQKRMGVQMQRFK (SEQ ID NO: 8)

GGAGCAAAAGCAGGGTGACAAAAACATAATGGATTCCAACACTGTGTCAAGCTT
TCAGGTAGACTGTTTTCTTTGGCATGTCCGCAAACGATTCGCAGACCAAGAACTG
GGTGATGCCCCATTCCTTGACCGGCTTCGCCGAGACCAGAAGTCCCTAAGGGGA
AGAGGTAGCACTCTTGGTCTGGACATCGAAACAGCCACTCATGCAGGAAAGCAG
ATAGTGGAGCAGATTCTGGAAAAGGAATCAGATGAGGCACTTAAAATGACCATT
GCCTCTGTTCCTGCTTCACGCTACTTAACTGACATGACTCTTGATGAGATGTCAAG
AGACTGGTTCATGCTCATGCCCAAGCAAAAAGTAACAGGCTCCCTATGTATAAG
AATGGACCAAGCAATCATGGATAAGAACATCATACTTAAAGCAAACTTTAGTGT
GATTTTCGAAAGGCTGGAAACACTAATACTACTTAGAGCCTTCACCGAAGAAGG
AGCAGTCGTTGGCGAAATTTCACCATTACCTTCTCTTCCAGGACATACTAATGAG
GATGTCAAAAATGCAATTGGGGTCCTCATCGGAGGACTTAAATGGAATGATAAT
ACGGTTAGAATCTCTGAAACTCTACAGAGATTCGCTTGGAGAAGCAGTCATGAA
AATGGGAGACCTTCATTCCCTTCAAAGCAGAAACGAAAAATGGAGAGAACAATT
AAGCCAGAAATTTGAAGAAATAAGATGGTTGATTGAAGAAGTGCGACATAGATT
GAAAAATACAGAAATAGTTTTGAACAAATAACATTTATGCAAGCCTTACAACT
ATTGCTTGAAGTAGAACAAGAGATAAGAACTTTCTCGTTTCAGCTTATTTAATGA
T (SEQ ID NO: 9)

FIG. 9

NS1 - Amino

MDSNTVSSFQVDCFLWHVRKRFADQELGDAPFLDRLRRDQKSLRGRGSTLGLDIET
ATHAGKQIVEQILEKESDEALKMTIASVPASRYLTDMTLDEMSRDWFMLMPKQKVT
GSLCIRMDQAIMDKNIILKANFSVIFERLETLILLRAFTEEGAVVGEISPLPSLPGHTNE
DVKNAIGVLIGGLKWNDNTVRISETLQRFAWRSSHENGRPSFPSKQKRKMERTIKPEI
(SEQ ID NO: 10)

FIG. 10

PA
TAAATGGAAGACTTTGTGCGACAGTGCTTCAATCCAATGATCGTCGAGCTTGCGG
AAAAGGCAATGAAAGAATATGGAGAGAACCCGAAAATCGAAACAAACAAATTT
GCAGCAATATGCACTCACTTGGAAGTCTGCTTCATGTACTCGGATTTCCACTTTAT
AAATGAACTGGGTGAGTCAGTGGTCATAGAGTCTGGTGACCCAAATGCTCTTTTG
AAACACAGATTTGAAATCATTGAGGGGAGAGATCGAACAATGGCATGGACAGTA
GTAAACAGCATCTGCAACACCACAAGAGCTGAAAAACCTAAATTTCTTCCAGATT
TATACGACTATAAGGAGAACAGATTTGTTGAAATTGGTGTGACAAGGAGAGAAG
TTCACATATACTACCTGGAGAAAGCCAACAAAATAAAGTCTGAGAAAACACATA
TCCACATTTTCTCATTTACAGGAGAAGAAATGGCTACAAAAGCGGACTATACTCT
TGATGAAGAGAGTAGAGCCAGGATCAAGACCAGACTATTCACTATAAGACAAGA
AATGGCCAGTAGAGGCCTCTGGGATTCCTTTCGTCAGTCCGAGAGAGGCGAAGA
GACAATTGAAGAAAGATTTGAAATCACAGGAACGATGCGCAAGCTTGCCAATTA
CAGTCTCCCACCGAACTTCTCCAGCCTTGAAAATTTTAGAGTCTATATAGATGGA
TTCGAACCGAACGGCTGCATTGAGAGTAAGCTTTCTCAAATGTCCAAAGAAGTA
AATGCCAAAATCGAACCATTTTCAAAGACAACACCCCGACCACTCAAAATGCCA
GGTGGTCCACCCTGCCATCAGCGATCCAAATTCTTGCtAATGGATGCTCTGAAACT
GAGCATTGAGGACCCAAGTCACGAGGGAGAGGGGATACCACTATATGATGCAAT
CAAATGCATGAAAACTTTCTTTGGATGGAAGAGCCCAGTATTGTTAAACCACAT
AAAAAGGGTATAAACCCGAACTATCTCCAAACTTGGAAGCAAGTATTAGAAGAA
ATACAAGACCTTGAGAACGAAGAAAGGACCCCAAGACCAAGAATATGAAAAA
AACAAGCCAATTGAAATGGGCACTAGGTGAAAATATGGCACCAGAGAAAGTGG
ATTTTGAGGATTGTAAAGACATCAATGATTTAAAACAATATGACAGTGATGAGCC
AGAAGCAAGGTCTCTTGCAAGTTGGATTCAAAGTGAGTTCAACAAGGCTTGTGA
GCTGACAGATTCAAGCTGGATAGAGCTCGATGAAATTGGGGAGGATGTCGCCCC
AATAGAATACATTGCGAGCATGAGGAGAAATTATTTTACTGCTGAGATTTCCCAT
TGTAGAGCAACAGAATATATAATGAAAGGAGTATACATCAACACTGCTCTACTC
AATGCATCCTGTGCTGCGATGGATGAATTTCAATTAATTCCGATGATAAGTAAAT
GCAGGACCAAAGAAGGGAGAAGGAAAACAAATTTATATGGATTCATAATAAAG
GGAAGGTCCCATTTAAGAAATGATACTGACGTGGTGAACTTTGTAAGTATGGAAT
TTTCTCTCACTGATCCAAGATTTGAGCCACACAAATGGGAAAAATACTGCGTTCT
AGAAATTGGAGACATGCTTCTAAGAACTGCTGTAGGTCAAGTGTCAAGACCCAT
ATTTTTGTATGTAAGGACAAATGGAACCTCTAAAATTAAAATGAAATGGGGAAT
GGAAATGAGACGCTGCCTCCTTCAGTCTCTGCAACAGATTGAAAGCATGATCGA
AGCTGAGTCCTCAGTCAAAGAAAAGGACATGACCAAAGAATTTTTTGAGAACAA
ATCAGAGACATGGCCTATAGGAGAGTCCCCCAAAGGAGTGGAAGAGGGCTCAAT
CGGGAAGGTTTGCAGGACCTTATTAGCAAAATCTGTGTTTAACAGTTTATATGCA
TCTCCACAACTGGAAGGATTTTCAGCTGAATCTAGGAAATTACTTCTCATTGTTC
AGGCTCTTAGAGATGACCTGGAACCTGGAACCTTTGATATTGGGGGGTTATATGA
ATCAATTGAGGAGTGCCTGATTAATGATCCCTGGGTTTTGCTTAATGCATCTTGGT
TCAACTCCTTCCTCACACATGCACTGAAGTAGTTGTGGCAATGCTACTATTTGTTA
TCCATACTGTCCA (SEQ ID NO: 11)

FIG. 11

PA - Amino

MEDFVRQCFNPMIVELAEKAMKEYGENPKIETNKFAAICTHLEVCFMYSDFHFINEL
GESVVIESGDPNALLKHRFEIIEGRDRTMAWTVVNSICNTTRAEKPKFLPDLYDYKEN
RFVEIGVTRREVHIYYLEKANKIKSEKTHIHIFSFTGEEMATKADYTLDEESRARIKTR
LFTIRQEMASRGLWDSFRQSERGEETIEERFEITGTMRKLANYSLPPNFSSLENFRVYI
DGFEPNGCIESKLSQMSKEVNAKIEPFSKTTPRPLKMPGGPPCHQRSKFLLMDALKLS
IEDPSHEGEGIPLYDAIKCMKTFFGWKEPSIVKPHKKGINPNYLQTWKQVLEEIQDLE
NEERTPKTKNMKKTSQLKWALGENMAPEKVDFEDCKDINDLKQYDSDEPEARSLAS
WIQSEFNKACELTDSSWIELDEIGEDVAPIEYIASMRRNYFTAEISHCRATEYIMKGVY
INTALLNASCAAMDEFQLIPMISKCRTKEGRRKTNLYGFIIKGRSHLRNDTDVVNFVS
MEFSLTDPRFEPHKWEKYCVLEIGDMLLRTAVGQVSRPIFLYVRTNGTSKIKMKWG
MEMRRCLLQSLQQIESMIEAESSVKEKDMTKEFFENKSETWPIGESPKGVEEGSIGKV
CRTLLAKSVFNSLYASPQLEGFSAESRKLLLIVQALRDDLEPGTFDIGGLYESIEECLIN
DPWVLLNASWFNSFLTHALK (SEQ ID NO: 12)

GAAAGCAGGCAAACCATTTGAATGGATGTCAATCCGACTCTACTTTTCTTAAAGG
TGCCAGCGCAAAATGCTATAAGCACAACATTCCCTTATACTGGAGATCCTCCCTA
CAGTCATGGAACAGGGACAGGATACACCATGGATACTGTCAACAGAACACACCA
ATATTCAGAAAAAGGGAAATGGACAACAAACACTGAGATTGGAGCACCACAACT
TAATCCAATCGATGGACCACTTCCTGAAGACAATGAACCAAGTGGGTACGCCCA
AACAGATTGTGTATTGGAAGCAATGGCTTTCCTTGAAGAATCCCATCCCGGAATC
TTTGAAAATTCGTGTCTTGAAACGATGGAGGTGATTCAGCAGACAAGAGTGGAC
AAACTAACACAAGGCCGACAAACTTATGATTGGACCTTGAATAGGAATCAACCT
GCCGCAACAGCACTTGCTAATACGATTGAAGTATTCAGATCAAATGGTCTGACTT
CCAATGAATCGGGGAGATTGATGGACTTCCTCAAAGATGTCATGGAGTCCATGA
ACAAGGAGGAAATGGAAATAACAACACACTTCCAACGGAAGAGAAGAGTAAGA
GACAACATGACAAAGAGAATGATAACACAGAGAACCATAGGGAAGAAAAAACA
ACGATTAAGCAGAAAGAGCTATCTAATCAGAACATTAACCCTAAACACAATGAC
CAAGGACGCTGAAAGAGGGAAATTGAAACGACGAGCAATCGCTACCCCAGGGA
TGCAGATAAGAGGATTTGTATATTTTGTTGAAACACTAGCTCGAAGAATATGTGA
AAAGCTTGAACAATCAGGATTGCCAGTTGGCGGTAATGAGAAAAAGGCCAAACT
GGCTAATGTCGTCAGAAAAATGATGACTAATTCCCAAGACACTGAACTCTCCTTC
ACCATCACTGGGGACAATACCAAATGGAATGAAAATCAGAACCCACGCATATTC
CTGGCAATGATCACATACATAACTAGAAATCAGCCAGAATGGTTCAGAAATGTT
CTAAGCATTGCACCGATTATGTTCTCAAATAAAATGGCAAGACTGGGGAAAGGA
TATATGTTTGAAAGCAAAAGTATGAAATTGAGAACTCAAATACCAGCAGAAATG
CTAGCAAGCATTGACCTAAAATATTTCAATGATTCAACAAAAAAGAAAATTGAA
AAGATACGACCACTCCTGGTTGACGGGACTGCTTCACTGAGTCCTGGCATGATGA
TGGGAATGTTCAACATGTTGAGCACTGTGCTGGGTGTATCCATATTAAACCTGGG
CCAGAGGAAATATACAAAGACCACATACTGGTGGGATGGTCTGCAATCATCCGA
TGACTTTGCTTTGATAGTGAATGCGCCTAATCATGAAGGAATACAAGCTGGAGTA
GACAGATTCTATAGAACTTGCAAACTGGTCGGGATCAACATGAGCAAAAGAAG
TCCTACATAAATAGAACTGGAACATTCGAATTCACAAGCTTTTTCTACCGGTATG
GTTTTGTAGCCAATTTCAGCATGGAACTACCCAGTTTTGGGGTTTCCGGAATAAA
TGAATCTGCAGACATGAGCATTGGAGTGACAGTCATCAAAAACAACATGATAAA
TAATGATCTCGGTCCTGCCACGGCACAAATGGYACTCCAACTCTTCATTAAGGAT
TATCGGTACACATACCGGTGCCATAGAGGTGATACCCAGATACAAACCAGAAGA
TCTTTTGAGTTGAAGAAACTGTGGGAACAGACTCGATCAAAGACTGGTCTACTGG
TATCAGATGGGGGTCCAAACCTATATAACATCAGAAACCTACACATCCCGGAAG
TCTGTTTAAAATGGGAGCTAATGGATGAAGATTATAAGGGGAGGCTATGCAATC
CATTGAATCCTTTCGTTAGTCACAAAGAAATTGAATCAGTCAACAGTGCAGTAGT
AATGCCTGCGCATGGCCCTGCCAAAAGCATGGAGTATGATGCTGTtGCAACAACA
CATTCTTGGATCCCCAAGAGGAACCGGTCCATATTGAACACAAGCCAAAGGGGA
ATACTAGAAGATGAGCAGATGTATCAGAAATGCTGCAACCTGTTTGAAAAATTCT
TCCCCAGCAGCTCATACAGAAGACCAGTCGGAATTTCTAGTATGGTTGAGGCCAT
GGTATCCAGGGCCCGCATTGATGCACGAATTGACTTCGAATCTGGACGGATAAA
GAAGGATGAGTTCGCTGAGATCATGAAGATCTGTTCCACCATTGAAGAGCTCAG
ACGGCAAAAATAGTGAA (SEQ ID NO: 13)

FIG. 13

PB1 - Amino

MDVNPTLLFLKVPAQNAISTTFPYTGDPPYSHGTGTGYTMDTVNRTHQYSEKGKWT
TNTEIGAPQLNPIDGPLPEDNEPSGYAQTDCVLEAMAFLEESHPGIFENSCLETMEVIQ
QTRVDKLTQGRQTYDWTLNRNQPAATALANTIEVFRSNGLTSNESGRLMDFLKDV
MESMNKEEMEITTHFQRKRRVRDNMTKRMITQRTIGKKKQRLSRKSYLIRTLTLNT
MTKDAERGKLKRRAIATPGMQIRGFVYFVETLARRICEKLEQSGLPVGGNEKKAKL
ANVVRKMMTNSQDTELSFTITGDNTKWNENQNPRIFLAMITYITRNQPEWFRNVLSI
APIMFSNKMARLGKGYMFESKSMKLRTQIPAEMLASIDLKYFNDSTKKKIEKIRPLLV
DGTASLSPGMMMGMFNMLSTVLGVSILNLGQRKYTKTTYWWDGLQSSDDFALIVN
APNHEGIQAGVDRFYRTCKLVGINMSKKKSYINRTGTFEFTSFFYRYGFVANFSMELP
SFGVSGINESADMSIGVTVIKNNMINNDLGPATAQMXLQLFIKDYRYTYRCHRGDTQ
IQTRRSFELKKLWEQTRSKTGLLVSDGGPNLYNIRNLHIPEVCLKWELMDEDYKGRL
CNPLNPFVSHKEIESVNSAVVMPAHGPAKSMEYDAVATTHSWIPKRNRSILNTSQRGI
LEDEQMYQKCCNLFEKFFPSSSYRRPVGISSMVEAMVSRARIDARIDFESGRIKKDEF
AEIMKICSTIEELRRQK (SEQ ID NO: 14)

FIG. 14

PB2
TATTGGTCTCAGGGAGCGAAAGCAGGTCAAATATATTCAATATGGAGAGAATAA
AAGAACTGAGAGATCTGATGTTACAATCCCGCACCCGCGAGATACTAACAAAAA
CTACTGTGGACCACATGGCCATAATCAAGAAATACACATCAGGAAGACAAGAGA
AGAACCCTGCACTTAGGATGAAATGGATGATGGCAATGAAATACCCAATTACAG
CAGATAAGAGGATAATGGAGATGATTCCTGAGAGAAATGAACAGGGACAAACC
CTTTGGAGCAAAACGAACGATGCTGGCTCAGACCGCGTAATGGTATCACCTCTGG
CAGTGACATGGTGGAATAGGAATGGACCAACAACGAACACAATTCATTATCCGA
AAGTCTACAAAACTTATTTTGAAAAGGTTGAAAGATTGAAACACGGAACCTTTG
GCCCCGTTCATTTTAGGAATCAAGTCAAGATAAGACGAAGAGTTGATGTAAACC
CTGGTCACGCGGACCTCAGTGCTAAAGAAGCACAAGATGTGATCATGGAAGTTG
TTTTCCCAAATGAAGTGGGAGCCAGAATTCTAACATCAGAATCACAACTAACAAT
AACCAAAGAGAAAAGGAAGAACTTCAGGACTGCAAAATTGCTCCCTTGATGGT
AGCATACATGCTAGAAAGAGAGTTGGTCCGAAAAACAAGGTTCCTCCCAGTAGT
AGGCGGAACAAGCAGTGTATACATTGAAGTGTTGCATCTGACTCAGGGAACATG
CTGGGAGCAAATGTACACCCCAGGAGGAGAAGTTAGAAACGATGATATTGATCA
AAGTTTAATTATTGCAGCCCGGAACATAGTGAGAAGAGCAACAGTATCAGCAGA
TCCACTAGCATCCCTACTGGAAATGTGCCACAGTACACAGATTGGTGGAACAAG
GATGGTAGACATCCTTAAGCAGAACCCAACAGAGGAACAAGCTGTGGATATATG
CAAAGCAGCAATGGGATTGAGAATTAGCTCATCATTCAGCTTTGGTGGATTCACC
TTCAAAAGGACAAGTGGATCATCAGTCAAGAGAGAAGAAGAAATGCTTACGGGC
AACCTTCAAACATTGAAAATAAGAGTGCATGAGGGCTATGAAGAATTCACAATG
GTCGGAAGAAGAGCAACAGCCATTATCAGAAAGGCAACCAGAAGATTGATTCAA
TTGATAGTAAGTGGGAGAGATGAACAATCAATTGCTGAAGCAATAATTGTAGCC
ATGGTGTTTTCGCAAGAAGATTGCATGATAAAAGCAGTTCGAGGCGATTTGAACT
TTGTTAATAGAGCAAATCAGCGTTTGAACCCCATGCATCAACTCTTGAGGCATTT
CCAAAAAGATGCAAAAGTGCTTTTCCAAAATTGGGGAATTGAACCCATCGACAA
TGTAATGGGGATGATTGGAATATTGCCTGACATGACCCCAAGCACCGAGATGTC
ATTGAGAGGAGTGAGAGTCAGCAAAATGGGAGTGGATGAGTACTCCAGCACTGA
GAGAGTGGTGGTGAGCATTGACCGTTTTTTAAGAGTTCGGGATCAAAGGGGAAA
CATACTACTGTCCCCTGAAGAAGTCAGTGAAACACAAGGAACGGAAAAGCTGAC
AATAATTTATTCGTCATCAATGATGTGGGAGATTAATGGTCCCGAATCAGTGTTG
GTCAATACTTATCAATGGATCATCAGAAACTGGGAAATTGTAAAAATTCAGTGGT
CACAGGACCCCACAATGTTATACAATAAGATAGAATTTGAACCATTCCAATCCCT
GGTCCCTAGGGCCACCAGAAGCCAATACAGCGGTTTCGTAAGAACCCTGTTTCAG
CAAATGCGAGATGTACTTGGAACATTTGATACTGCTCAAATAATAAAACTCCTCC
CTTTTGCCGCTGCTCCTCCGGAACAGAGTAGGATGCAGTTCTCTTCTTTGACTGTT
AATGTAAGAGGTTCGGGAATGAGGATACTTGTAAGAGGCAATTCCCCGGTGTTC
AACTACAATAAAGTCACTAAAAGGCTCACAGTCCTCGGAAAGGATGCAGGTGCG
CTTACTGAGGACCCAGATGAAGGTACGGCTGGAGTAGAATCTGCTGTTCTAAGA
GGGTTTCTCATTTTAGGTAAAGAAAACAAGAGATATGGCCCAGCACTAAGCATC
AATGAACTTAGCAAACTTGCAAAAGGGGAGAAAGCCAATGTACTAATTGGGCAA
GGGGACGTAGTGTTGGTAATGAAACGGAAACGTGACTCTAGCATACTTACTGAC
AGCCAGACAGCGACCAAAAGGATTCGGATGGCCATCAATTAGTGTTGAATTGTTT
AAAAACGACCTTGTTTCTACTAATACGAGACCATAT (SEQ ID NO: 15)

FIG. 15

PB2 - Amino

MERIKELRDLMLQSRTREILTKTTVDHMAIIKKYTSGRQEKNPALRMKWMMAMKY
PITADKRIMEMIPERNEQGQTLWSKTNDAGSDRVMVSPLAVTWWNRNGPTTNTIHY
PKVYKTYFEKVERLKHGTFGPVHFRNQVKIRRRVDVNPGHADLSAKEAQDVIMEVV
FPNEVGARILTSESQLTITKEKKEELQDCKIAPLMVAYMLERELVRKTRFLPVVGGTS
SVYIEVLHLTQGTCWEQMYTPGGEVRNDDIDQSLIIAARNIVRRATVSADPLASLLE
MCHSTQIGGTRMVDILKQNPTEEQAVDICKAAMGLRISSSFSFGGFTFKRTSGSSVKR
EEEMLTGNLQTLKIRVHEGYEEFTMVGRRATAIIRKATRRLIQLIVSGRDEQSIAEAII
VAMVFSQEDCMIKAVRGDLNFVNRANQRLNPMHQLLRHFQKDAKVLFQNWGIEPI
DNVMGMIGILPDMTPSTEMSLRGVRVSKMGVDEYSSTERVVVSIDRFLRVRDQRGNI
LLSPEEVSETQGTEKLTIIYSSSMMWEINGPESVLVNTYQWIIRNWEIVKIQWSQDPT
MLYNKIEFEPFQSLVPRATRSQYSGFVRTLFQQMRDVLGTFDTAQIIKLLPFAAAPPE
QSRMQFSSLTVNVRGSGMRILVRGNSPVFNYNKVTKRLTVLGKDAGALTEDPDEGT
AGVESAVLRGFLILGKENKRYGPALSINELSKLAKGEKANVLIGQGDVVLVMKRKR
DSSILTDSQTATKRIRMAIN (SEQ ID NO: 16)

FIG. 16

SEQUENCE LISTING

```
<160> NUMBER OF SEQ ID NOS: 16

<210> SEQ ID NO 1
<211> LENGTH: 1450
<212> TYPE: DNA
<213> ORGANISM: Influenza A virus
<220> FEATURE:
<221> NAME/KEY: CDS
<222> LOCATION: (9)..(1418)

<400> SEQUENCE: 1 agtttaaa atg aat cca aat caa aag ata ata gca att gga ttt gca tca          50
         Met Asn Pro Asn Gln Lys Ile Ile Ala Ile Gly Phe Ala Ser
         1               5                   10 ttg ggg ata tta atc att aat gtc att ctc cat gta gtc agc att ata          98
Leu Gly Ile Leu Ile Ile Asn Val Ile Leu His Val Val Ser Ile Ile
15                  20                  25                  30 gta aca gta ctg gtc ctc aat aac aat aga aca gat ctg aac tgc aaa         146
Val Thr Val Leu Val Leu Asn Asn Asn Arg Thr Asp Leu Asn Cys Lys
                35                  40                  45 ggg acg atc ata aga gaa tac aat gaa aca gta aga gta gaa aaa ctt         194
Gly Thr Ile Ile Arg Glu Tyr Asn Glu Thr Val Arg Val Glu Lys Leu
            50                  55                  60 act caa tgg tat aat acc agt aca att aag tac ata gag aga cct tca         242
Thr Gln Trp Tyr Asn Thr Ser Thr Ile Lys Tyr Ile Glu Arg Pro Ser
        65                  70                  75 aat gaa tac tac atg aat aac act gaa cca ctt tgt gag gcc caa ggc         290
Asn Glu Tyr Tyr Met Asn Asn Thr Glu Pro Leu Cys Glu Ala Gln Gly
    80                  85                  90 ttt gca cca ttt tcc aaa gat aat gga ata cga att ggg tcg aga ggc         338
Phe Ala Pro Phe Ser Lys Asp Asn Gly Ile Arg Ile Gly Ser Arg Gly
95                  100                 105                 110
```

```
cat gtt ttt gtg ata aga gaa cct ttt gta tca tgt tcg ccc tca gaa       386
His Val Phe Val Ile Arg Glu Pro Phe Val Ser Cys Ser Pro Ser Glu
                115                 120                 125 tgt aga acc ttt ttc ctc aca cag ggc tca tta ctc aat gac aaa cat       434
Cys Arg Thr Phe Phe Leu Thr Gln Gly Ser Leu Leu Asn Asp Lys His
            130                 135                 140 tct aac ggc aca ata aag gat cga agc ccg tat agg act ttg atg agt       482
Ser Asn Gly Thr Ile Lys Asp Arg Ser Pro Tyr Arg Thr Leu Met Ser
        145                 150                 155 gtc aaa ata ggg caa tca ccc aat gta tat caa gct agg ttt gaa tcg       530
Val Lys Ile Gly Gln Ser Pro Asn Val Tyr Gln Ala Arg Phe Glu Ser
    160                 165                 170 gtg gca tgg tca gca aca gca tgc cat gat gga aaa aaa tgg atg aca       578
Val Ala Trp Ser Ala Thr Ala Cys His Asp Gly Lys Lys Trp Met Thr
175                 180                 185                 190 gtt gga gtc aca ggg ccc gac aat caa gca att gca gta gtg aac tat       626
Val Gly Val Thr Gly Pro Asp Asn Gln Ala Ile Ala Val Val Asn Tyr
                195                 200                 205 gga ggt gtt ccg gtt gat act att aat tca tgg gca ggg gat att tta       674
Gly Gly Val Pro Val Asp Thr Ile Asn Ser Trp Ala Gly Asp Ile Leu
            210                 215                 220 aga acc caa gaa tca tca tgc acc tgc att aaa gga gac tgt tat tgg       722
Arg Thr Gln Glu Ser Ser Cys Thr Cys Ile Lys Gly Asp Cys Tyr Trp
        225                 230                 235 gta atg act gat gga ccg gca aat agg caa gct aaa tat agg ata ttc       770
Val Met Thr Asp Gly Pro Ala Asn Arg Gln Ala Lys Tyr Arg Ile Phe
    240                 245                 250 aaa gca aaa gat gga aga gta att gga caa act gat ata agt ttc aat       818
Lys Ala Lys Asp Gly Arg Val Ile Gly Gln Thr Asp Ile Ser Phe Asn
255                 260                 265                 270 ggg gga cac ata gag gag tgt tct tgt tac ccc aat gaa ggg aag gtg       866
Gly Gly His Ile Glu Glu Cys Ser Cys Tyr Pro Asn Glu Gly Lys Val
                275                 280                 285 gaa tgc ata tgc agg gac aat tgg act gga aca aat aga cca att ctg       914
Glu Cys Ile Cys Arg Asp Asn Trp Thr Gly Thr Asn Arg Pro Ile Leu
            290                 295                 300 gta ata tct tct gat cta tcg tac aca gtt gga tat ttg tgt gct ggc       962
Val Ile Ser Ser Asp Leu Ser Tyr Thr Val Gly Tyr Leu Cys Ala Gly
        305                 310                 315 att ccc act gac act cct agg gga gag gat agt caa ttc aca ggc tca      1010
Ile Pro Thr Asp Thr Pro Arg Gly Glu Asp Ser Gln Phe Thr Gly Ser
    320                 325                 330 tgt aca agt cct ttg gga aat aaa gga tac ggt gta aaa ggc ttc ggg      1058
Cys Thr Ser Pro Leu Gly Asn Lys Gly Tyr Gly Val Lys Gly Phe Gly
335                 340                 345                 350 ttt cga caa gga act gac gta tgg gcc gga agg aca att agt agg act      1106
Phe Arg Gln Gly Thr Asp Val Trp Ala Gly Arg Thr Ile Ser Arg Thr
                355                 360                 365 tca aga tca gga ttc gaa ata ata aaa tca agg aat ggt tgg aca cag      1154
Ser Arg Ser Gly Phe Glu Ile Ile Lys Ile Arg Asn Gly Trp Thr Gln
            370                 375                 380 aac agt aag gac caa atc agg agg caa gtg att atc gat gac cca aat      1202
Asn Ser Lys Asp Gln Ile Arg Arg Gln Val Ile Ile Asp Asp Pro Asn
        385                 390                 395 tgg tca gga tat agc ggt tct ttc aca ttg ccg gtt gaa ctg aca aaa      1250
Trp Ser Gly Tyr Ser Gly Ser Phe Thr Leu Pro Val Glu Leu Thr Lys
    400                 405                 410 aag gga tgt ttg gtc ccc tgt ttc tgg gtt gaa atg att aga ggt aaa      1298
Lys Gly Cys Leu Val Pro Cys Phe Trp Val Glu Met Ile Arg Gly Lys
415                 420                 425                 430
```

```
cct gaa gaa aca aca ata tgg acc tct agc agc tcc att gtg atg tgt    1346
Pro Glu Glu Thr Thr Ile Trp Thr Ser Ser Ser Ser Ile Val Met Cys
                435                 440                 445 gga gta gat cat aaa att gcc agt tgg tca tgg cac gat gga gct att    1394
Gly Val Asp His Lys Ile Ala Ser Trp Ser Trp His Asp Gly Ala Ile
            450                 455                 460 ctt ccc ttt gac atc gat aag atg taatttacga aaaaaactcc ttgtttctac   1448
Leu Pro Phe Asp Ile Asp Lys Met
        465                 470 ta                                                                 1450

<210> SEQ ID NO 2
<211> LENGTH: 470
<212> TYPE: PRT
<213> ORGANISM: Influenza A virus

<400> SEQUENCE: 2

Met Asn Pro Asn Gln Lys Ile Ile Ala Ile Gly Phe Ala Ser Leu Gly
1               5                   10                  15

Ile Leu Ile Ile Asn Val Ile Leu His Val Val Ser Ile Ile Val Thr
            20                  25                  30

Val Leu Val Leu Asn Asn Asn Arg Thr Asp Leu Asn Cys Lys Gly Thr
        35                  40                  45

Ile Ile Arg Glu Tyr Asn Glu Thr Val Arg Val Glu Lys Leu Thr Gln
    50                  55                  60

Trp Tyr Asn Thr Ser Thr Ile Lys Tyr Ile Glu Arg Pro Ser Asn Glu
65                  70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Ser Glu Cys Arg
        115                 120                 125

Thr Phe Phe Leu Thr Gln Gly Ser Leu Leu Asn Asp Lys His Ser Asn
    130                 135                 140

Gly Thr Ile Lys Asp Arg Ser Pro Tyr Arg Thr Leu Met Ser Val Lys
145                 150                 155                 160

Ile Gly Gln Ser Pro Asn Val Tyr Gln Ala Arg Phe Glu Ser Val Ala
                165                 170                 175

Trp Ser Ala Thr Ala Cys His Asp Gly Lys Lys Trp Met Thr Val Gly
            180                 185                 190

Val Thr Gly Pro Asp Asn Gln Ala Ile Ala Val Val Asn Tyr Gly Gly
        195                 200                 205

Val Pro Val Asp Thr Ile Asn Ser Trp Ala Gly Asp Ile Leu Arg Thr
    210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Lys Tyr Arg Ile Phe Lys Ala
                245                 250                 255

Lys Asp Gly Arg Val Ile Gly Gln Thr Asp Ile Ser Phe Asn Gly Gly
            260                 265                 270

His Ile Glu Glu Cys Ser Cys Tyr Pro Asn Glu Gly Lys Val Glu Cys
        275                 280                 285

Ile Cys Arg Asp Asn Trp Thr Gly Thr Asn Arg Pro Ile Leu Val Ile
    290                 295                 300
```

```
Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
            325                 330                 335

Ser Pro Leu Gly Asn Lys Gly Tyr Gly Val Lys Gly Phe Gly Phe Arg
                340                 345                 350

Gln Gly Thr Asp Val Trp Ala Gly Arg Thr Ile Ser Arg Thr Ser Arg
        355                 360                 365

Ser Gly Phe Glu Ile Ile Lys Ile Arg Asn Gly Trp Thr Gln Asn Ser
    370                 375                 380

Lys Asp Gln Ile Arg Arg Gln Val Ile Ile Asp Pro Asn Trp Ser
385                 390                 395                 400

Gly Tyr Ser Gly Ser Phe Thr Leu Pro Val Glu Leu Thr Lys Lys Gly
                405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ile Val Met Cys Gly Val
                435                 440                 445

Asp His Lys Ile Ala Ser Trp Ser Trp His Asp Gly Ala Ile Leu Pro
        450                 455                 460

Phe Asp Ile Asp Lys Met
465                 470

<210> SEQ ID NO 3
<211> LENGTH: 1762
<212> TYPE: DNA
<213> ORGANISM: Influenza A Virus
<220> FEATURE:
<221> NAME/KEY: CDS
<222> LOCATION: (30)..(1724)

<400> SEQUENCE: 3
agcaaaagca ggggatattt ctgtcaatc atg aag aca acc att att tta ata       53
                                 Met Lys Thr Thr Ile Ile Leu Ile
                                 1               5 cta ctg acc cat tgg gcc tac agt caa aac cca atc agt ggc aat aac      101
Leu Leu Thr His Trp Ala Tyr Ser Gln Asn Pro Ile Ser Gly Asn Asn
    10                  15                  20 aca gcc aca ctg tgt ctg gga cac cat gca gta gca aat gga aca ttg      149
Thr Ala Thr Leu Cys Leu Gly His His Ala Val Ala Asn Gly Thr Leu
25                  30                  35                  40 gta aaa aca atg agt gat gat caa att gag gtg aca aat gct aca gaa      197
Val Lys Thr Met Ser Asp Asp Gln Ile Glu Val Thr Asn Ala Thr Glu
                45                  50                  55 tta gtt cag agc att tca atg ggg aaa ata tgc aac aaa tca tat aga      245
Leu Val Gln Ser Ile Ser Met Gly Lys Ile Cys Asn Lys Ser Tyr Arg
            60                  65                  70 att cta gat gga aga aat tgc aca tta ata gat gca atg cta gga gac      293
Ile Leu Asp Gly Arg Asn Cys Thr Leu Ile Asp Ala Met Leu Gly Asp
        75                  80                  85 ccc cac tgt gac gcc ctt cag tat gag agt tgg gac ctc ttt ata gaa      341
Pro His Cys Asp Ala Leu Gln Tyr Glu Ser Trp Asp Leu Phe Ile Glu
    90                  95                  100 aga agc agc gct ttc agc aat tgc tac cca tat gac atc cct gac tat      389
Arg Ser Ser Ala Phe Ser Asn Cys Tyr Pro Tyr Asp Ile Pro Asp Tyr
105                 110                 115                 120 gca tcg ctc cga tcc att gta gca tcc tca gga aca gtt gaa ttc aca      437
Ala Ser Leu Arg Ser Ile Val Ala Ser Ser Gly Thr Val Glu Phe Thr
                125                 130                 135
```

```
gca gag gga ttc aca tgg aca ggt gta act caa aac gga aga agt gga      485
Ala Glu Gly Phe Thr Trp Thr Gly Val Thr Gln Asn Gly Arg Ser Gly
            140                 145                 150 gcc tgc aaa agg gga tca gcc gat agt ttc ttt agc cga ctg aat tgg      533
Ala Cys Lys Arg Gly Ser Ala Asp Ser Phe Phe Ser Arg Leu Asn Trp
        155                 160                 165 cta aca aaa tct gga agc tct tac ccc aca ttg aat gtg aca atg cct      581
Leu Thr Lys Ser Gly Ser Ser Tyr Pro Thr Leu Asn Val Thr Met Pro
    170                 175                 180 aac aat aaa aat ttc gac aag cta tac atc tgg ggg att cat cac ccg      629
Asn Asn Lys Asn Phe Asp Lys Leu Tyr Ile Trp Gly Ile His His Pro
185                 190                 195                 200 agc tca aat caa gag cag aca aaa ttg tac atc caa gaa tca gga cga      677
Ser Ser Asn Gln Glu Gln Thr Lys Leu Tyr Ile Gln Glu Ser Gly Arg
            205                 210                 215 gta aca gtc tca aca aaa aga agt caa caa aca ata atc cct aac atc      725
Val Thr Val Ser Thr Lys Arg Ser Gln Gln Thr Ile Ile Pro Asn Ile
        220                 225                 230 gaa tct aga ccg ttg gtc aga ggt caa tca ggc agg ata agc ata tac      773
Glu Ser Arg Pro Leu Val Arg Gly Gln Ser Gly Arg Ile Ser Ile Tyr
    235                 240                 245 tgg acc att gta aaa cct gga gat atc cta atg ata aac agt aat ggc      821
Trp Thr Ile Val Lys Pro Gly Asp Ile Leu Met Ile Asn Ser Asn Gly
250                 255                 260 aac tta gtt gca ccg cgg gga tat ttt aaa ttg aac aca ggg aaa agc      869
Asn Leu Val Ala Pro Arg Gly Tyr Phe Lys Leu Asn Thr Gly Lys Ser
265                 270                 275                 280 tct gta atg aga tcc gat gta ccc ata gac att tgt gtg tct gaa tgt      917
Ser Val Met Arg Ser Asp Val Pro Ile Asp Ile Cys Val Ser Glu Cys
            285                 290                 295 att aca cca aat gga agc atc tcc aac gac aag cca ttc caa aat gtg      965
Ile Thr Pro Asn Gly Ser Ile Ser Asn Asp Lys Pro Phe Gln Asn Val
        300                 305                 310 aac aaa gtt aca tat gga aaa tgc ccc aag tat atc agg caa aac act     1013
Asn Lys Val Thr Tyr Gly Lys Cys Pro Lys Tyr Ile Arg Gln Asn Thr
    315                 320                 325 tta aag ctg gcc act ggg atg agg aat gta cca gaa aag caa acc aga     1061
Leu Lys Leu Ala Thr Gly Met Arg Asn Val Pro Glu Lys Gln Thr Arg
330                 335                 340 gga atc ttt gga gca ata gcg gga ttc atc gaa aac ggc tgg gaa gga     1109
Gly Ile Phe Gly Ala Ile Ala Gly Phe Ile Glu Asn Gly Trp Glu Gly
345                 350                 355                 360 atg gtt gat ggg tgg tat ggg ttc cga tat caa aac tct gaa gga aca     1157
Met Val Asp Gly Trp Tyr Gly Phe Arg Tyr Gln Asn Ser Glu Gly Thr
            365                 370                 375 ggg caa gct gca gat cta aag agc act caa gca gcc att gac cag att     1205
Gly Gln Ala Ala Asp Leu Lys Ser Thr Gln Ala Ala Ile Asp Gln Ile
        380                 385                 390 aat gga aag tta aac aga gtg att gaa aga acc aat gag aaa ttc cat     1253
Asn Gly Lys Leu Asn Arg Val Ile Glu Arg Thr Asn Glu Lys Phe His
    395                 400                 405 caa ata gag aag gaa ttc tca gaa gta gaa gga aga att cag gac ttg     1301
Gln Ile Glu Lys Glu Phe Ser Glu Val Glu Gly Arg Ile Gln Asp Leu
410                 415                 420 gag aaa tat gta gaa gac acc aaa ata gac cta tgg tcc tac aat gca     1349
Glu Lys Tyr Val Glu Asp Thr Lys Ile Asp Leu Trp Ser Tyr Asn Ala
425                 430                 435                 440 gaa ttg ctg gtg gct cta gaa aat caa cat aca att gac tta aca gat     1397
Glu Leu Leu Val Ala Leu Glu Asn Gln His Thr Ile Asp Leu Thr Asp
            445                 450                 455
```

-continued

```
gca gaa atg aat aaa tta ttt gag aag act aga cgc cag tta aga gaa    1445
Ala Glu Met Asn Lys Leu Phe Glu Lys Thr Arg Arg Gln Leu Arg Glu
        460                 465                 470 aac gca gaa gac atg gga ggt gga tgt ttc aag att tac cac aaa tgt    1493
Asn Ala Glu Asp Met Gly Gly Gly Cys Phe Lys Ile Tyr His Lys Cys
475                 480                 485 gat aat gca tgc att gaa tca ata aga act ggg aca tat gac cat tac    1541
Asp Asn Ala Cys Ile Glu Ser Ile Arg Thr Gly Thr Tyr Asp His Tyr
        490                 495                 500 ata tac aga gat gaa gca tta aac aac cga ttt cag atc aaa ggt gta    1589
Ile Tyr Arg Asp Glu Ala Leu Asn Asn Arg Phe Gln Ile Lys Gly Val
505                 510                 515                 520 gag ttg aaa tca ggc tac aaa gat tgg ata ctg tgg att tca ttc gcc    1637
Glu Leu Lys Ser Gly Tyr Lys Asp Trp Ile Leu Trp Ile Ser Phe Ala
                525                 530                 535 ata tca tgc ttc tta att tgc gtt gtt cta ttg ggt ttc att atg tgg    1685
Ile Ser Cys Phe Leu Ile Cys Val Val Leu Leu Gly Phe Ile Met Trp
        540                 545                 550 gct tgc caa aaa ggc aac atc aga tgc aac att tgc att tgagtaaact    1734
Ala Cys Gln Lys Gly Asn Ile Arg Cys Asn Ile Cys Ile
555                 560                 565 gatagttaaa aacacccttg tttctact                                     1762

<210> SEQ ID NO 4
<211> LENGTH: 565
<212> TYPE: PRT
<213> ORGANISM: Influenza A Virus

<400> SEQUENCE: 4

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
                20                  25                  30

His Ala Val Ala Asn Gly Thr Leu Val Lys Thr Met Ser Asp Asp Gln
            35                  40                  45

Ile Glu Val Thr Asn Ala Thr Glu Leu Val Gln Ser Ile Ser Met Gly
        50                  55                  60

Lys Ile Cys Asn Lys Ser Tyr Arg Ile Leu Asp Gly Arg Asn Cys Thr
65                  70                  75                  80

Leu Ile Asp Ala Met Leu Gly Asp Pro His Cys Asp Ala Leu Gln Tyr
                85                  90                  95

Glu Ser Trp Asp Leu Phe Ile Glu Arg Ser Ser Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Val Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
    210                 215                 220
```

```
Gln Gln Thr Ile Ile Pro Asn Ile Glu Ser Arg Pro Leu Val Arg Gly
225                 230                 235                 240

Gln Ser Gly Arg Ile Ser Ile Tyr Trp Thr Ile Val Lys Pro Gly Asp
            245                 250                 255

Ile Leu Met Ile Asn Ser Asn Gly Asn Leu Val Ala Pro Arg Gly Tyr
        260                 265                 270

Phe Lys Leu Asn Thr Gly Lys Ser Ser Val Met Arg Ser Asp Val Pro
    275                 280                 285

Ile Asp Ile Cys Val Ser Glu Cys Ile Thr Pro Asn Gly Ser Ile Ser
290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
            325                 330                 335

Asn Val Pro Glu Lys Gln Thr Arg Gly Ile Phe Gly Ala Ile Ala Gly
        340                 345                 350

Phe Ile Glu Asn Gly Trp Glu Gly Met Val Asp Gly Trp Tyr Gly Phe
    355                 360                 365

Arg Tyr Gln Asn Ser Glu Gly Thr Gly Gln Ala Ala Asp Leu Lys Ser
370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
            405                 410                 415

Val Glu Gly Arg Ile Gln Asp Leu Glu Lys Tyr Val Glu Asp Thr Lys
        420                 425                 430

Ile Asp Leu Trp Ser Tyr Asn Ala Glu Leu Leu Val Ala Leu Glu Asn
    435                 440                 445

Gln His Thr Ile Asp Leu Thr Asp Ala Glu Met Asn Lys Leu Phe Glu
450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Glu Ser Ile
            485                 490                 495

Arg Thr Gly Thr Tyr Asp His Tyr Ile Tyr Arg Asp Glu Ala Leu Asn
        500                 505                 510

Asn Arg Phe Gln Ile Lys Gly Val Glu Leu Lys Ser Gly Tyr Lys Asp
    515                 520                 525

Trp Ile Leu Trp Ile Ser Phe Ala Ile Ser Cys Phe Leu Ile Cys Val
530                 535                 540

Val Leu Leu Gly Phe Ile Met Trp Ala Cys Gln Lys Gly Asn Ile Arg
545                 550                 555                 560

Cys Asn Ile Cys Ile
            565
```

<210> SEQ ID NO 5
<211> LENGTH: 1585
<212> TYPE: DNA
<213> ORGANISM: Influenza A Virus
<220> FEATURE:
<221> NAME/KEY: CDS
<222> LOCATION: (51)..(1544

<400> SEQUENCE: 5

```
cagggagcaa aagcaggta gataatcact cactgagtga catcaaagtc atg gcg          56
                                                        Met Ala
                                                          1 tct caa ggc acc aaa cga tcc tat gaa cag atg gaa act gat ggg gaa       104
Ser Gln Gly Thr Lys Arg Ser Tyr Glu Gln Met Glu Thr Asp Gly Glu
         5                  10                  15 cgc cag aat gca act gaa atc aga gca tct gtc gga agg atg gtg gga       152
Arg Gln Asn Ala Thr Glu Ile Arg Ala Ser Val Gly Arg Met Val Gly
 20                  25                  30 gga atc gga cgg ttt tat gtc cag atg tgt act gag ctt aaa cta aac       200
Gly Ile Gly Arg Phe Tyr Val Gln Met Cys Thr Glu Leu Lys Leu Asn
 35                  40                  45                  50 gac cat gaa ggg cgg ctg att cag aac agc ata aca ata gaa agg atg       248
Asp His Glu Gly Arg Leu Ile Gln Asn Ser Ile Thr Ile Glu Arg Met
             55                  60                  65 gta ctt tca gca ttc gac gaa aga aga aac aag tat ctc gag gag cat       296
Val Leu Ser Ala Phe Asp Glu Arg Arg Asn Lys Tyr Leu Glu Glu His
         70                  75                  80 ccc agt gct ggg aaa gac cct aag aaa acg gga ggc ccg ata tac aga       344
Pro Ser Ala Gly Lys Asp Pro Lys Lys Thr Gly Gly Pro Ile Tyr Arg
     85                  90                  95 aga aaa gat ggg aaa tgg atg agg gaa ctc atc ctc cat gat aaa gaa       392
Arg Lys Asp Gly Lys Trp Met Arg Glu Leu Ile Leu His Asp Lys Glu
100                 105                 110 gaa atc atg aga atc tgg cgt cag gcc aac aat ggt gaa gac gct act       440
Glu Ile Met Arg Ile Trp Arg Gln Ala Asn Asn Gly Glu Asp Ala Thr
115                 120                 125                 130 gct ggt ctt act cat atg atg atc tgg cac tcc aat ctc aat gac acc       488
Ala Gly Leu Thr His Met Met Ile Trp His Ser Asn Leu Asn Asp Thr
                135                 140                 145 aca tac caa aga aca agg gct ctt gtt cgg act ggg atg gat ccc aga       536
Thr Tyr Gln Arg Thr Arg Ala Leu Val Arg Thr Gly Met Asp Pro Arg
            150                 155                 160 atg tgc tct ctg atg caa ggc tca acc ctc cca cgg aga tct gga gcc       584
Met Cys Ser Leu Met Gln Gly Ser Thr Leu Pro Arg Arg Ser Gly Ala
            165                 170                 175 gct ggt gct gca gta aaa ggt gtt gga aca atg gta atg gaa ctc atc       632
Ala Gly Ala Ala Val Lys Gly Val Gly Thr Met Val Met Glu Leu Ile
180                 185                 190 agg atg atc aaa cgc gga ata aat gat cgg aat ttc tgg aga ggt gaa       680
Arg Met Ile Lys Arg Gly Ile Asn Asp Arg Asn Phe Trp Arg Gly Glu
195                 200                 205                 210 aat ggt cga aga acc aga att gct tat gaa aga atg tgc aat atc ctc       728
Asn Gly Arg Arg Thr Arg Ile Ala Tyr Glu Arg Met Cys Asn Ile Leu
                215                 220                 225 aaa ggg aaa ttt cag aca gca gca caa cgg gct atg atg gac cag gtg       776
Lys Gly Lys Phe Gln Thr Ala Ala Gln Arg Ala Met Met Asp Gln Val
            230                 235                 240 agg gaa ggc cgc aat cct gga aac gct gag att gag gat ctc att ttc       824
Arg Glu Gly Arg Asn Pro Gly Asn Ala Glu Ile Glu Asp Leu Ile Phe
            245                 250                 255 ttg gca cga tca gca ctt att ttg aga gga tca gta gcc cat aaa tca       872
Leu Ala Arg Ser Ala Leu Ile Leu Arg Gly Ser Val Ala His Lys Ser
260                 265                 270 tgc cta cct gcc tgt gtt tat ggc ctt gca gta acc agt ggg tat gac       920
Cys Leu Pro Ala Cys Val Tyr Gly Leu Ala Val Thr Ser Gly Tyr Asp
275                 280                 285                 290
```

-continued

```
ttt gag aag gaa gga tac tct ctg gtt gga att gat cct ttc aaa cta      968
Phe Glu Lys Glu Gly Tyr Ser Leu Val Gly Ile Asp Pro Phe Lys Leu
                295                 300                 305 ctc cag aac agt caa att ttc agt cta atc aga cca aaa gaa aac cca     1016
Leu Gln Asn Ser Gln Ile Phe Ser Leu Ile Arg Pro Lys Glu Asn Pro
            310                 315                 320 gca cac aaa agc cag ttg gtg tgg atg gca tgc cat tct gca gca ttt     1064
Ala His Lys Ser Gln Leu Val Trp Met Ala Cys His Ser Ala Ala Phe
        325                 330                 335 gag gat ctg aga gtt tta aat ttc att aga gga acc aaa gta atc cca     1112
Glu Asp Leu Arg Val Leu Asn Phe Ile Arg Gly Thr Lys Val Ile Pro
    340                 345                 350 aga gga cag tta aca acc aga gga gtt caa att gct tca aat gaa aac     1160
Arg Gly Gln Leu Thr Thr Arg Gly Val Gln Ile Ala Ser Asn Glu Asn
355                 360                 365                 370 atg gag aca ata aat tct agc aca ctt gaa ctg aga agc aaa tat tgg     1208
Met Glu Thr Ile Asn Ser Ser Thr Leu Glu Leu Arg Ser Lys Tyr Trp
                375                 380                 385 gca ata agg acc aga agc gga gga aac acc agt caa cag aga gca ttt     1256
Ala Ile Arg Thr Arg Ser Gly Gly Asn Thr Ser Gln Gln Arg Ala Phe
            390                 395                 400 gca gga cag ata agt gtg caa cct act ttc tca gta cag aga aat ctt     1304
Ala Gly Gln Ile Ser Val Gln Pro Thr Phe Ser Val Gln Arg Asn Leu
        405                 410                 415 ccc ttt gag aga gca acc att atg gct gca ttc act ggt aac act gaa     1352
Pro Phe Glu Arg Ala Thr Ile Met Ala Ala Phe Thr Gly Asn Thr Glu
    420                 425                 430 ggg agg act tcc gac atg aga acg gaa atc ata agg atg atg gaa aat     1400
Gly Arg Thr Ser Asp Met Arg Thr Glu Ile Ile Arg Met Met Glu Asn
435                 440                 445                 450 gcc aaa tca gaa gat gtg tct ttc cag ggg cgg gga gtc ttc gag ctc     1448
Ala Lys Ser Glu Asp Val Ser Phe Gln Gly Arg Gly Val Phe Glu Leu
                455                 460                 465 tcg gac gaa aag gca acg aac ccg atc gtg cct tcc ttt gac atg agc     1496
Ser Asp Glu Lys Ala Thr Asn Pro Ile Val Pro Ser Phe Asp Met Ser
            470                 475                 480 aat gaa ggg tct tat ttc ttc gga gac aat gct gag gag ttt gac agt     1544
Asn Glu Gly Ser Tyr Phe Phe Gly Asp Asn Ala Glu Glu Phe Asp Ser
        485                 490                 495 taaagaaaaa tacccttgtt tctactaata cgagacgata t                       1585

<210> SEQ ID NO 6
<211> LENGTH: 498
<212> TYPE: PRT
<213> ORGANISM: Influenza A Virus

<400> SEQUENCE: 6

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Val Gln Met Cys Thr Glu Leu Lys
        35                  40                  45

Leu Asn Asp His Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95
```

-continued

```
Tyr Arg Arg Lys Asp Gly Lys Trp Met Arg Glu Leu Ile Leu His Asp
            100                 105                 110
Lys Glu Glu Ile Met Arg Ile Trp Arg Gln Ala Asn Gly Glu Asp
        115                 120                 125
Ala Thr Ala Gly Leu Thr His Met Met Ile Trp His Ser Asn Leu Asn
    130                 135                 140
Asp Thr Thr Tyr Gln Arg Thr Arg Ala Leu Val Arg Thr Gly Met Asp
145                 150                 155                 160
Pro Arg Met Cys Ser Leu Met Gln Gly Ser Thr Leu Pro Arg Arg Ser
                165                 170                 175
Gly Ala Ala Gly Ala Ala Val Lys Gly Val Gly Thr Met Val Met Glu
            180                 185                 190
Leu Ile Arg Met Ile Lys Arg Gly Ile Asn Asp Arg Asn Phe Trp Arg
        195                 200                 205
Gly Glu Asn Gly Arg Arg Thr Arg Ile Ala Tyr Glu Arg Met Cys Asn
    210                 215                 220
Ile Leu Lys Gly Lys Phe Gln Thr Ala Ala Gln Arg Ala Met Met Asp
225                 230                 235                 240
Gln Val Arg Glu Gly Arg Asn Pro Gly Asn Ala Glu Ile Glu Asp Leu
                245                 250                 255
Ile Phe Leu Ala Arg Ser Ala Leu Ile Leu Arg Gly Ser Val Ala His
            260                 265                 270
Lys Ser Cys Leu Pro Ala Cys Val Tyr Gly Leu Ala Val Thr Ser Gly
        275                 280                 285
Tyr Asp Phe Glu Lys Glu Gly Tyr Ser Leu Val Gly Ile Asp Pro Phe
    290                 295                 300
Lys Leu Leu Gln Asn Ser Gln Ile Phe Ser Leu Ile Arg Pro Lys Glu
305                 310                 315                 320
Asn Pro Ala His Lys Ser Gln Leu Val Trp Met Ala Cys His Ser Ala
                325                 330                 335
Ala Phe Glu Asp Leu Arg Val Leu Asn Phe Ile Arg Gly Thr Lys Val
            340                 345                 350
Ile Pro Arg Gly Gln Leu Thr Thr Arg Gly Val Gln Ile Ala Ser Asn
        355                 360                 365
Glu Asn Met Glu Thr Ile Asn Ser Ser Thr Leu Glu Leu Arg Ser Lys
    370                 375                 380
Tyr Trp Ala Ile Arg Thr Arg Ser Gly Gly Asn Thr Ser Gln Gln Arg
385                 390                 395                 400
Ala Phe Ala Gly Gln Ile Ser Val Gln Pro Thr Phe Ser Val Gln Arg
                405                 410                 415
Asn Leu Pro Phe Glu Arg Ala Thr Ile Met Ala Ala Phe Thr Gly Asn
            420                 425                 430
Thr Glu Gly Arg Thr Ser Asp Met Arg Thr Glu Ile Ile Arg Met Met
        435                 440                 445
Glu Asn Ala Lys Ser Glu Asp Val Ser Phe Gln Gly Arg Gly Val Phe
    450                 455                 460
Glu Leu Ser Asp Glu Lys Ala Thr Asn Pro Ile Val Pro Ser Phe Asp
465                 470                 475                 480
Met Ser Asn Glu Gly Ser Tyr Phe Phe Gly Asp Asn Ala Glu Glu Phe
                485                 490                 495
Asp Ser
```

```
<210> SEQ ID NO 7
<211> LENGTH: 1056
<212> TYPE: DNA
<213> ORGANISM: Influenza A virus
<220> FEATURE:
<221> NAME/KEY: CDS
<222> LOCATION: (40)..(795)

<400> SEQUENCE: 7
tattcgtctc agggagcaaa agcaggtaga tatttaaag atg agt ctt cta acc        54
                                            Met Ser Leu Leu Thr
                                            1               5 gag gtc gaa acg tac gtt ctc tct atc gta cca tca ggc ccc ctc aaa      102
Glu Val Glu Thr Tyr Val Leu Ser Ile Val Pro Ser Gly Pro Leu Lys
            10                  15                  20 gcc gag atc gcg cag aga ctt gaa gat gtc ttt gcg gga aag aac acc     150
Ala Glu Ile Ala Gln Arg Leu Glu Asp Val Phe Ala Gly Lys Asn Thr
        25                  30                  35 gat ctt gag gca ctc atg gaa tgg cta aag aca aga cca atc ctg tca      198
Asp Leu Glu Ala Leu Met Glu Trp Leu Lys Thr Arg Pro Ile Leu Ser
    40                  45                  50 cct ctg act aaa ggg att tta gga ttt gta ttc acg ctc acc gtg ccc      246
Pro Leu Thr Lys Gly Ile Leu Gly Phe Val Phe Thr Leu Thr Val Pro
55                  60                  65 agt gag cga gga ctg cag cgt aga cgc ttt gtc caa aat gcc ctt agt      294
Ser Glu Arg Gly Leu Gln Arg Arg Arg Phe Val Gln Asn Ala Leu Ser
70                  75                  80                  85 gga aac gga gat cca aac aac atg gac aga gca gta aaa ctg tac agg      342
Gly Asn Gly Asp Pro Asn Asn Met Asp Arg Ala Val Lys Leu Tyr Arg
                90                  95                  100 aag ctt aaa aga gaa ata aca ttc cat gag gca aaa gag gtg gca ctc      390
Lys Leu Lys Arg Glu Ile Thr Phe His Glu Ala Lys Glu Val Ala Leu
            105                 110                 115 agc tat tcc act ggt gca cta gcc agc tgc atg gga ctc ata tac aac      438
Ser Tyr Ser Thr Gly Ala Leu Ala Ser Cys Met Gly Leu Ile Tyr Asn
        120                 125                 130 aga atg gga act gtt aca acc gaa gtg gca ttt ggc ctg gta tgc gcc      486
Arg Met Gly Thr Val Thr Thr Glu Val Ala Phe Gly Leu Val Cys Ala
    135                 140                 145 aca tgt gaa cag att gct gat tcc cag cat cga tct cac agg cag atg      534
Thr Cys Glu Gln Ile Ala Asp Ser Gln His Arg Ser His Arg Gln Met
150                 155                 160                 165 gtg aca aca acc aac cca tta atc aga cat gaa aac aga atg gta tta      582
Val Thr Thr Thr Asn Pro Leu Ile Arg His Glu Asn Arg Met Val Leu
                170                 175                 180 gcc agt acc acg gct aaa gcc atg gaa cag atg gca gga tcg agt gag      630
Ala Ser Thr Thr Ala Lys Ala Met Glu Gln Met Ala Gly Ser Ser Glu
            185                 190                 195 cag gca gca gag gcc atg gag gtt gct agt agg gct agg cag atg gta      678
Gln Ala Ala Glu Ala Met Glu Val Ala Ser Arg Ala Arg Gln Met Val
        200                 205                 210 cag gca atg aga acc att ggg acc cac cct agc tcc agt gcc ggt ttg      726
Gln Ala Met Arg Thr Ile Gly Thr His Pro Ser Ser Ser Ala Gly Leu
    215                 220                 225 aaa gat gat ctc ctt gaa aat tta cag gcc tac cag aaa cgg atg gga      774
Lys Asp Asp Leu Leu Glu Asn Leu Gln Ala Tyr Gln Lys Arg Met Gly
230                 235                 240                 245 gtg caa atg cag cga ttc aag tgatcctctc gttattgcag caagtatcat        825
Val Gln Met Gln Arg Phe Lys
                250
```

```
tggaatcttg cacttgatat tgtggattct tgatcgtctt ttcttcaaat tcatttatcg      885
tcgccttaaa tacgggttga aaagagggcc ttctacggaa ggagtacctg agtctatgag      945
ggaagaatat cggcaggaac agcagaatgc tgtggatgtt gacgatggtc attttgtcaa     1005
catagagctg gagtaaaaaa ctaccttgtt tctactaata cgagacgata t              1056
```

<210> SEQ ID NO 8
<211> LENGTH: 252
<212> TYPE: PRT
<213> ORGANISM: Influenza A virus

<400> SEQUENCE: 8

```
Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Glu Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Arg
        195                 200                 205

Ala Arg Gln Met Val Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250
```

<210> SEQ ID NO 9
<211> LENGTH: 870
<212> TYPE: DNA
<213> ORGANISM: Influenza A virus
<220> FEATURE:
<221> NAME/KEY: CDS
<222> LOCATION: (29)..(718)

<400> SEQUENCE: 9

```
ggagcaaaag cagggtgaca aaaacata atg gat tcc aac act gtg tca agc        52
                                Met Asp Ser Asn Thr Val Ser Ser
                                1               5
```

-continued

| | | |
|---|---|---|
| ttt cag gta gac tgt ttt ctt tgg cat gtc cgc aaa cga ttc gca gac<br>Phe Gln Val Asp Cys Phe Leu Trp His Val Arg Lys Arg Phe Ala Asp<br>     10                          15                      20 | 100 | |
| caa gaa ctg ggt gat gcc cca ttc ctt gac cgg ctt cgc cga gac cag<br>Gln Glu Leu Gly Asp Ala Pro Phe Leu Asp Arg Leu Arg Arg Asp Gln<br> 25                    30                    35                    40 | 148 | |
| aag tcc cta agg gga aga ggt agc act ctt ggt ctg gac atc gaa aca<br>Lys Ser Leu Arg Gly Arg Gly Ser Thr Leu Gly Leu Asp Ile Glu Thr<br>                    45                        50                        55 | 196 | |
| gcc act cat gca gga aag cag ata gtg gag cag att ctg gaa aag gaa<br>Ala Thr His Ala Gly Lys Gln Ile Val Glu Gln Ile Leu Glu Lys Glu<br>               60                        65                        70 | 244 | |
| tca gat gag gca ctt aaa atg acc att gcc tct gtt cct gct tca cgc<br>Ser Asp Glu Ala Leu Lys Met Thr Ile Ala Ser Val Pro Ala Ser Arg<br> 75                    80                    85 | 292 | |
| tac tta act gac atg act ctt gat gag atg tca aga gac tgg ttc atg<br>Tyr Leu Thr Asp Met Thr Leu Asp Glu Met Ser Arg Asp Trp Phe Met<br>          90                       95                      100 | 340 | |
| ctc atg ccc aag caa aaa gta aca ggc tcc cta tgt ata aga atg gac<br>Leu Met Pro Lys Gln Lys Val Thr Gly Ser Leu Cys Ile Arg Met Asp<br>105                       110                    115                    120 | 388 | |
| caa gca atc atg gat aag aac atc ata ctt aaa gca aac ttt agt gtg<br>Gln Ala Ile Met Asp Lys Asn Ile Ile Leu Lys Ala Asn Phe Ser Val<br>                         125                    130                    135 | 436 | |
| att ttc gaa agg ctg gaa aca cta ata cta ctt aga gcc ttc acc gaa<br>Ile Phe Glu Arg Leu Glu Thr Leu Ile Leu Leu Arg Ala Phe Thr Glu<br>               140                        145                    150 | 484 | |
| gaa gga gca gtc gtt ggc gaa att tca cca tta cct tct ctt cca gga<br>Glu Gly Ala Val Val Gly Glu Ile Ser Pro Leu Pro Ser Leu Pro Gly<br>          155                       160                    165 | 532 | |
| cat act aat gag gat gtc aaa aat gca att ggg gtc ctc atc gga gga<br>His Thr Asn Glu Asp Val Lys Asn Ala Ile Gly Val Leu Ile Gly Gly<br>170                       175                    180 | 580 | |
| ctt aaa tgg aat gat aat acg gtt aga atc tct gaa act cta cag aga<br>Leu Lys Trp Asn Asp Asn Thr Val Arg Ile Ser Glu Thr Leu Gln Arg<br>185                       190                    195                    200 | 628 | |
| ttc gct tgg aga agc agt cat gaa aat ggg aga cct tca ttc cct tca<br>Phe Ala Trp Arg Ser Ser His Glu Asn Gly Arg Pro Ser Phe Pro Ser<br>               205                        210                    215 | 676 | |
| aag cag aaa cga aaa atg gag aga aca att aag cca gaa att<br>Lys Gln Lys Arg Lys Met Glu Arg Thr Ile Lys Pro Glu Ile<br>        220                       225                    230 | 718 | |
| tgaagaaata agatggttga ttgaagaagt gcgacataga ttgaaaaata cagaaaatag | 778 | |
| ttttgaacaa ataacattta tgcaagcctt acaactattg cttgaagtag aacaagagat | 838 | |
| aagaactttc tcgtttcagc ttatttaatg at | 870 | |

<210> SEQ ID NO 10
<211> LENGTH: 230
<212> TYPE: PRT
<213> ORGANISM: Influenza A virus

<400> SEQUENCE: 10

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly

```
Thr Leu Gly Leu Asp Ile Glu Thr Ala Thr His Ala Gly Lys Gln Ile
    50                  55                  60

Val Glu Gln Ile Leu Glu Lys Glu Ser Asp Glu Ala Leu Lys Met Thr
 65                  70                  75                  80

Ile Ala Ser Val Pro Ala Ser Arg Tyr Leu Thr Asp Met Thr Leu Asp
                 85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
            115                 120                 125

Ile Leu Lys Ala Asn Phe Ser Val Ile Phe Glu Arg Leu Glu Thr Leu
    130                 135                 140

Ile Leu Leu Arg Ala Phe Thr Glu Glu Gly Ala Val Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Lys Trp Asn Asp Asn Thr Val
            180                 185                 190

Arg Ile Ser Glu Thr Leu Gln Arg Phe Ala Trp Arg Ser Ser His Glu
            195                 200                 205

Asn Gly Arg Pro Ser Phe Pro Ser Lys Gln Lys Arg Lys Met Glu Arg
    210                 215                 220

Thr Ile Lys Pro Glu Ile
225                 230

<210> SEQ ID NO 11
<211> LENGTH: 2191
<212> TYPE: DNA
<213> ORGANISM: Influenza A virus
<220> FEATURE:
<221> NAME/KEY: CDS
<222> LOCATION: (4)..(2151)

<400> SEQUENCE: 11 taa atg gaa gac ttt gtg cga cag tgc ttc aat cca atg atc gtc gag      48
    Met Glu Asp Phe Val Arg Gln Cys Phe Asn Pro Met Ile Val Glu
     1               5                  10                  15 ctt gcg gaa aag gca atg aaa gaa tat gga gag aac ccg aaa atc gaa      96
Leu Ala Glu Lys Ala Met Lys Glu Tyr Gly Glu Asn Pro Lys Ile Glu
             20                  25                  30 aca aac aaa ttt gca gca ata tgc act cac ttg gaa gtc tgc ttc atg     144
Thr Asn Lys Phe Ala Ala Ile Cys Thr His Leu Glu Val Cys Phe Met
         35                  40                  45 tac tcg gat ttc cac ttt ata aat gaa ctg ggt gag tca gtg gtc ata     192
Tyr Ser Asp Phe His Phe Ile Asn Glu Leu Gly Glu Ser Val Val Ile
     50                  55                  60 gag tct ggt gac cca aat gct ctt ttg aaa cac aga ttt gaa atc att     240
Glu Ser Gly Asp Pro Asn Ala Leu Leu Lys His Arg Phe Glu Ile Ile
 65                  70                  75 gag ggg aga gat cga aca atg gca tgg aca gta gta aac agc atc tgc     288
Glu Gly Arg Asp Arg Thr Met Ala Trp Thr Val Val Asn Ser Ile Cys
 80                  85                  90                  95 aac acc aca aga gct gaa aaa cct aaa ttt ctt cca gat tta tac gac     336
Asn Thr Thr Arg Ala Glu Lys Pro Lys Phe Leu Pro Asp Leu Tyr Asp
                100                 105                 110 tat aag gag aac aga ttt gtt gaa att ggt gtg aca agg aga gaa gtt     384
Tyr Lys Glu Asn Arg Phe Val Glu Ile Gly Val Thr Arg Arg Glu Val
            115                 120                 125
```

```
cac ata tac tac ctg gag aaa gcc aac aaa ata aag tct gag aaa aca        432
His Ile Tyr Tyr Leu Glu Lys Ala Asn Lys Ile Lys Ser Glu Lys Thr
        130                 135                 140 cat atc cac att ttc tca ttt aca gga gaa gaa atg gct aca aaa gcg        480
His Ile His Ile Phe Ser Phe Thr Gly Glu Glu Met Ala Thr Lys Ala
145                 150                 155 gac tat act ctt gat gaa gag agt aga gcc agg atc aag acc aga cta        528
Asp Tyr Thr Leu Asp Glu Glu Ser Arg Ala Arg Ile Lys Thr Arg Leu
160                 165                 170                 175 ttc act ata aga caa gaa atg gcc agt aga ggc ctc tgg gat tcc ttt        576
Phe Thr Ile Arg Gln Glu Met Ala Ser Arg Gly Leu Trp Asp Ser Phe
            180                 185                 190 cgt cag tcc gag aga ggc gaa gag aca att gaa gaa aga ttt gaa atc        624
Arg Gln Ser Glu Arg Gly Glu Glu Thr Ile Glu Glu Arg Phe Glu Ile
                195                 200                 205 aca gga acg atg cgc aag ctt gcc aat tac agt ctc cca ccg aac ttc        672
Thr Gly Thr Met Arg Lys Leu Ala Asn Tyr Ser Leu Pro Pro Asn Phe
                    210                 215                 220 tcc agc ctt gaa aat ttt aga gtc tat ata gat gga ttc gaa ccg aac        720
Ser Ser Leu Glu Asn Phe Arg Val Tyr Ile Asp Gly Phe Glu Pro Asn
    225                 230                 235 ggc tgc att gag agt aag ctt tct caa atg tcc aaa gaa gta aat gcc        768
Gly Cys Ile Glu Ser Lys Leu Ser Gln Met Ser Lys Glu Val Asn Ala
240                 245                 250                 255 aaa atc gaa cca ttt tca aag aca aca ccc cga cca ctc aaa atg cca        816
Lys Ile Glu Pro Phe Ser Lys Thr Thr Pro Arg Pro Leu Lys Met Pro
                    260                 265                 270 ggt ggt cca ccc tgc cat cag cga tcc aaa ttc ttg cta atg gat gct        864
Gly Gly Pro Pro Cys His Gln Arg Ser Lys Phe Leu Leu Met Asp Ala
                275                 280                 285 ctg aaa ctg agc att gag gac cca agt cac gag gga gag ggg ata cca        912
Leu Lys Leu Ser Ile Glu Asp Pro Ser His Glu Gly Glu Gly Ile Pro
            290                 295                 300 cta tat gat gca atc aaa tgc atg aaa act ttc ttt gga tgg aaa gag        960
Leu Tyr Asp Ala Ile Lys Cys Met Lys Thr Phe Phe Gly Trp Lys Glu
        305                 310                 315 ccc agt att gtt aaa cca cat aaa aag ggt ata aac ccg aac tat ctc       1008
Pro Ser Ile Val Lys Pro His Lys Lys Gly Ile Asn Pro Asn Tyr Leu
320                 325                 330                 335 caa act tgg aag caa gta tta gaa gaa ata caa gac ctt gag aac gaa       1056
Gln Thr Trp Lys Gln Val Leu Glu Glu Ile Gln Asp Leu Glu Asn Glu
                340                 345                 350 gaa agg acc ccc aag acc aag aat atg aaa aaa aca agc caa ttg aaa       1104
Glu Arg Thr Pro Lys Thr Lys Asn Met Lys Lys Thr Ser Gln Leu Lys
                355                 360                 365 tgg gca cta ggt gaa aat atg gca cca gag aaa gtg gat ttt gag gat       1152
Trp Ala Leu Gly Glu Asn Met Ala Pro Glu Lys Val Asp Phe Glu Asp
            370                 375                 380 tgt aaa gac atc aat gat tta aaa caa tat gac agt gat gag cca gaa       1200
Cys Lys Asp Ile Asn Asp Leu Lys Gln Tyr Asp Ser Asp Glu Pro Glu
        385                 390                 395 gca agg tct ctt gca agt tgg att caa agt gag ttc aac aag gct tgt       1248
Ala Arg Ser Leu Ala Ser Trp Ile Gln Ser Glu Phe Asn Lys Ala Cys
400                 405                 410                 415 gag ctg aca gat tca agc tgg ata gag ctc gat gaa att ggg gag gat       1296
Glu Leu Thr Asp Ser Ser Trp Ile Glu Leu Asp Glu Ile Gly Glu Asp
                420                 425                 430 gtc gcc cca ata gaa tac att gcg agc atg agg aga aat tat ttt act       1344
Val Ala Pro Ile Glu Tyr Ile Ala Ser Met Arg Arg Asn Tyr Phe Thr
                435                 440                 445
```

-continued

```
gct gag att tcc cat tgt aga gca aca gaa tat ata atg aaa gga gta      1392
Ala Glu Ile Ser His Cys Arg Ala Thr Glu Tyr Ile Met Lys Gly Val
        450                 455                 460 tac atc aac act gct cta ctc aat gca tcc tgt gct gcg atg gat gaa      1440
Tyr Ile Asn Thr Ala Leu Leu Asn Ala Ser Cys Ala Ala Met Asp Glu
    465                 470                 475 ttt caa tta att ccg atg ata agt aaa tgc agg acc aaa gaa ggg aga      1488
Phe Gln Leu Ile Pro Met Ile Ser Lys Cys Arg Thr Lys Glu Gly Arg
480                 485                 490                 495 agg aaa aca aat tta tat gga ttc ata ata aag gga agg tcc cat tta      1536
Arg Lys Thr Asn Leu Tyr Gly Phe Ile Ile Lys Gly Arg Ser His Leu
                500                 505                 510 aga aat gat act gac gtg gtg aac ttt gta agt atg gaa ttt tct ctc      1584
Arg Asn Asp Thr Asp Val Val Asn Phe Val Ser Met Glu Phe Ser Leu
            515                 520                 525 act gat cca aga ttt gag cca cac aaa tgg gaa aaa tac tgc gtt cta      1632
Thr Asp Pro Arg Phe Glu Pro His Lys Trp Glu Lys Tyr Cys Val Leu
        530                 535                 540 gaa att gga gac atg ctt cta aga act gct gta ggt caa gtg tca aga      1680
Glu Ile Gly Asp Met Leu Leu Arg Thr Ala Val Gly Gln Val Ser Arg
    545                 550                 555 ccc ata ttt ttg tat gta agg aca aat gga acc tct aaa att aaa atg      1728
Pro Ile Phe Leu Tyr Val Arg Thr Asn Gly Thr Ser Lys Ile Lys Met
560                 565                 570                 575 aaa tgg gga atg gaa atg aga cgc tgc ctc ctt cag tct ctg caa cag      1776
Lys Trp Gly Met Glu Met Arg Arg Cys Leu Leu Gln Ser Leu Gln Gln
                580                 585                 590 att gaa agc atg atc gaa gct gag tcc tca gtc aaa gaa aag gac atg      1824
Ile Glu Ser Met Ile Glu Ala Glu Ser Ser Val Lys Glu Lys Asp Met
            595                 600                 605 acc aaa gaa ttt ttt gag aac aaa tca gag aca tgg cct ata gga gag      1872
Thr Lys Glu Phe Phe Glu Asn Lys Ser Glu Thr Trp Pro Ile Gly Glu
        610                 615                 620 tcc ccc aaa gga gtg gaa gag ggc tca atc ggg aag gtt tgc agg acc      1920
Ser Pro Lys Gly Val Glu Glu Gly Ser Ile Gly Lys Val Cys Arg Thr
    625                 630                 635 tta tta gca aaa tct gtg ttt aac agt tta tat gca tct cca caa ctg      1968
Leu Leu Ala Lys Ser Val Phe Asn Ser Leu Tyr Ala Ser Pro Gln Leu
640                 645                 650                 655 gaa gga ttt tca gct gaa tct agg aaa tta ctt ctc att gtt cag gct      2016
Glu Gly Phe Ser Ala Glu Ser Arg Lys Leu Leu Leu Ile Val Gln Ala
                660                 665                 670 ctt aga gat gac ctg gaa cct gga acc ttt gat att ggg ggg tta tat      2064
Leu Arg Asp Asp Leu Glu Pro Gly Thr Phe Asp Ile Gly Gly Leu Tyr
            675                 680                 685 gaa tca att gag gag tgc ctg att aat gat ccc tgg gtt ttg ctt aat      2112
Glu Ser Ile Glu Glu Cys Leu Ile Asn Asp Pro Trp Val Leu Leu Asn
        690                 695                 700 gca tct tgg ttc aac tcc ttc ctc aca cat gca ctg aag tagttgtggc       2161
Ala Ser Trp Phe Asn Ser Phe Leu Thr His Ala Leu Lys
    705                 710                 715 aatgctacta tttgttatcc atactgtcca                                     2191
```

<210> SEQ ID NO 12
<211> LENGTH: 716
<212> TYPE: PRT
<213> ORGANISM: Influenza A virus

<400> SEQUENCE: 12

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asn Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Leu Gly Glu Ser Val Val Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Arg Ala Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
            115                 120                 125

Ile Tyr Tyr Leu Glu Lys Ala Asn Lys Ile Lys Ser Glu Lys Thr His
130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
            195                 200                 205

Gly Thr Met Arg Lys Leu Ala Asn Tyr Ser Leu Pro Pro Asn Phe Ser
210                 215                 220

Ser Leu Glu Asn Phe Arg Val Tyr Ile Asp Gly Phe Glu Pro Asn Gly
225                 230                 235                 240

Cys Ile Glu Ser Lys Leu Ser Gln Met Ser Lys Glu Val Asn Ala Lys
                245                 250                 255

Ile Glu Pro Phe Ser Lys Thr Thr Pro Arg Pro Leu Lys Met Pro Gly
            260                 265                 270

Gly Pro Pro Cys His Gln Arg Ser Lys Phe Leu Leu Met Asp Ala Leu
            275                 280                 285

Lys Leu Ser Ile Glu Asp Pro Ser His Glu Gly Glu Gly Ile Pro Leu
290                 295                 300

Tyr Asp Ala Ile Lys Cys Met Lys Thr Phe Phe Gly Trp Lys Glu Pro
305                 310                 315                 320

Ser Ile Val Lys Pro His Lys Lys Gly Ile Asn Pro Asn Tyr Leu Gln
                325                 330                 335

Thr Trp Lys Gln Val Leu Glu Glu Ile Gln Asp Leu Glu Asn Glu Glu
            340                 345                 350

Arg Thr Pro Lys Thr Lys Asn Met Lys Lys Thr Ser Gln Leu Lys Trp
            355                 360                 365

Ala Leu Gly Glu Asn Met Ala Pro Glu Lys Val Asp Phe Glu Asp Cys
370                 375                 380

Lys Asp Ile Asn Asp Leu Lys Gln Tyr Asp Ser Asp Glu Pro Glu Ala
385                 390                 395                 400

Arg Ser Leu Ala Ser Trp Ile Gln Ser Glu Phe Asn Lys Ala Cys Glu
                405                 410                 415
```

```
Leu Thr Asp Ser Ser Trp Ile Glu Leu Asp Glu Ile Gly Glu Asp Val
            420                 425                 430

Ala Pro Ile Glu Tyr Ile Ala Ser Met Arg Arg Asn Tyr Phe Thr Ala
            435                 440                 445

Glu Ile Ser His Cys Arg Ala Thr Glu Tyr Ile Met Lys Gly Val Tyr
            450                 455                 460

Ile Asn Thr Ala Leu Leu Asn Ala Ser Cys Ala Ala Met Asp Glu Phe
465                 470                 475                 480

Gln Leu Ile Pro Met Ile Ser Lys Cys Arg Thr Lys Glu Gly Arg Arg
            485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
            515                 520                 525

Asp Pro Arg Phe Glu Pro His Lys Trp Glu Lys Tyr Cys Val Leu Glu
            530                 535                 540

Ile Gly Asp Met Leu Leu Arg Thr Ala Val Gly Gln Val Ser Arg Pro
545                 550                 555                 560

Ile Phe Leu Tyr Val Arg Thr Asn Gly Thr Ser Lys Ile Lys Met Lys
            565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
            595                 600                 605

Lys Glu Phe Phe Glu Asn Lys Ser Glu Thr Trp Pro Ile Gly Glu Ser
            610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
            645                 650                 655

Gly Phe Ser Ala Glu Ser Arg Lys Leu Leu Leu Ile Val Gln Ala Leu
            660                 665                 670

Arg Asp Asp Leu Glu Pro Gly Thr Phe Asp Ile Gly Gly Leu Tyr Glu
            675                 680                 685

Ser Ile Glu Glu Cys Leu Ile Asn Asp Pro Trp Val Leu Leu Asn Ala
690                 695                 700

Ser Trp Phe Asn Ser Phe Leu Thr His Ala Leu Lys
705                 710                 715

<210> SEQ ID NO 13
<211> LENGTH: 2299
<212> TYPE: DNA
<213> ORGANISM: Influenza A virus
<220> FEATURE:
<221> NAME/KEY: CDS
<222> LOCATION: (22)..(2292)
<220> FEATURE:
<221> NAME/KEY: misc_feature
<222> LOCATION: (547)..(547)
<223> OTHER INFORMATION: Xaa stands for Ala or Val

<400> SEQUENCE: 13
gaaagcaggc aaaccatttg a atg gat gtc aat ccg act cta ctt ttc tta       51
                        Met Asp Val Asn Pro Thr Leu Leu Phe Leu
                          1               5                  10 aag gtg cca gcg caa aat gct ata agc aca aca ttc cct tat act gga       99
Lys Val Pro Ala Gln Asn Ala Ile Ser Thr Thr Phe Pro Tyr Thr Gly
            15                  20                  25
```

|     |     |
| --- | --- |
| gat cct ccc tac agt cat gga aca ggg aca gga tac acc atg gat act<br>Asp Pro Pro Tyr Ser His Gly Thr Gly Thr Gly Tyr Thr Met Asp Thr<br>30                  35                  40 | 147 |
| gtc aac aga aca cac caa tat tca gaa aaa ggg aaa tgg aca aca aac<br>Val Asn Arg Thr His Gln Tyr Ser Glu Lys Gly Lys Trp Thr Thr Asn<br>    45                  50                  55 | 195 |
| act gag att gga gca cca caa ctt aat cca atc gat gga cca ctt cct<br>Thr Glu Ile Gly Ala Pro Gln Leu Asn Pro Ile Asp Gly Pro Leu Pro<br>60                  65                  70 | 243 |
| gaa gac aat gaa cca agt ggg tac gcc caa aca gat tgt gta ttg gaa<br>Glu Asp Asn Glu Pro Ser Gly Tyr Ala Gln Thr Asp Cys Val Leu Glu<br>75                  80                  85                  90 | 291 |
| gca atg gct ttc ctt gaa gaa tcc cat ccc gga atc ttt gaa aat tcg<br>Ala Met Ala Phe Leu Glu Glu Ser His Pro Gly Ile Phe Glu Asn Ser<br>                95                  100                 105 | 339 |
| tgt ctt gaa acg atg gag gtg att cag cag aca aga gtg gac aaa cta<br>Cys Leu Glu Thr Met Glu Val Ile Gln Gln Thr Arg Val Asp Lys Leu<br>                110                 115                 120 | 387 |
| aca caa ggc cga caa act tat gat tgg acc ttg aat agg aat caa cct<br>Thr Gln Gly Arg Gln Thr Tyr Asp Trp Thr Leu Asn Arg Asn Gln Pro<br>            125                 130                 135 | 435 |
| gcc gca aca gca ctt gct aat acg att gaa gta ttc aga tca aat ggt<br>Ala Ala Thr Ala Leu Ala Asn Thr Ile Glu Val Phe Arg Ser Asn Gly<br>140                 145                 150 | 483 |
| ctg act tcc aat gaa tcg ggg aga ttg atg gac ttc ctc aaa gat gtc<br>Leu Thr Ser Asn Glu Ser Gly Arg Leu Met Asp Phe Leu Lys Asp Val<br>155                 160                 165                 170 | 531 |
| atg gag tcc atg aac aag gag gaa atg gaa ata aca aca cac ttc caa<br>Met Glu Ser Met Asn Lys Glu Glu Met Glu Ile Thr Thr His Phe Gln<br>                175                 180                 185 | 579 |
| cgg aag aga aga gta aga gac aac atg aca aag aga atg ata aca cag<br>Arg Lys Arg Arg Val Arg Asp Asn Met Thr Lys Arg Met Ile Thr Gln<br>                190                 195                 200 | 627 |
| aga acc ata ggg aag aaa aaa caa cga tta agc aga aag agc tat cta<br>Arg Thr Ile Gly Lys Lys Lys Gln Arg Leu Ser Arg Lys Ser Tyr Leu<br>            205                 210                 215 | 675 |
| atc aga aca tta acc cta aac aca atg acc aag gac gct gaa aga ggg<br>Ile Arg Thr Leu Thr Leu Asn Thr Met Thr Lys Asp Ala Glu Arg Gly<br>220                 225                 230 | 723 |
| aaa ttg aaa cga cga gca atc gct acc cca ggg atg cag ata aga gga<br>Lys Leu Lys Arg Arg Ala Ile Ala Thr Pro Gly Met Gln Ile Arg Gly<br>235                 240                 245                 250 | 771 |
| ttt gta tat ttt gtt gaa aca cta gct cga aga ata tgt gaa aag ctt<br>Phe Val Tyr Phe Val Glu Thr Leu Ala Arg Arg Ile Cys Glu Lys Leu<br>                255                 260                 265 | 819 |
| gaa caa tca gga ttg cca gtt ggc ggt aat gag aaa aag gcc aaa ctg<br>Glu Gln Ser Gly Leu Pro Val Gly Gly Asn Glu Lys Lys Ala Lys Leu<br>                270                 275                 280 | 867 |
| gct aat gtc gtc aga aaa atg atg act aat tcc caa gac act gaa ctc<br>Ala Asn Val Val Arg Lys Met Met Thr Asn Ser Gln Asp Thr Glu Leu<br>            285                 290                 295 | 915 |
| tcc ttc acc atc act ggg gac aat acc aaa tgg aat gaa aat cag aac<br>Ser Phe Thr Ile Thr Gly Asp Asn Thr Lys Trp Asn Glu Asn Gln Asn<br>300                 305                 310 | 963 |
| cca cgc ata ttc ctg gca atg atc aca tac ata act aga aat cag cca<br>Pro Arg Ile Phe Leu Ala Met Ile Thr Tyr Ile Thr Arg Asn Gln Pro<br>315                 320                 325                 330 | 1011 |
| gaa tgg ttc aga aat gtt cta agc att gca ccg att atg ttc tca aat<br>Glu Trp Phe Arg Asn Val Leu Ser Ile Ala Pro Ile Met Phe Ser Asn<br>                335                 340                 345 | 1059 |

```
                                              -continued aaa atg gca aga ctg ggg aaa gga tat atg ttt gaa agc aaa agt atg      1107
Lys Met Ala Arg Leu Gly Lys Gly Tyr Met Phe Glu Ser Lys Ser Met
        350                 355                 360 aaa ttg aga act caa ata cca gca gaa atg cta gca agc att gac cta      1155
Lys Leu Arg Thr Gln Ile Pro Ala Glu Met Leu Ala Ser Ile Asp Leu
        365                 370                 375 aaa tat ttc aat gat tca aca aaa aag aaa att gaa aag ata cga cca      1203
Lys Tyr Phe Asn Asp Ser Thr Lys Lys Lys Ile Glu Lys Ile Arg Pro
        380                 385                 390 ctc ctg gtt gac ggg act gct tca ctg agt cct ggc atg atg atg gga      1251
Leu Leu Val Asp Gly Thr Ala Ser Leu Ser Pro Gly Met Met Met Gly
395                 400                 405                 410 atg ttc aac atg ttg agc act gtg ctg ggt gta tcc ata tta aac ctg      1299
Met Phe Asn Met Leu Ser Thr Val Leu Gly Val Ser Ile Leu Asn Leu
                415                 420                 425 ggc cag agg aaa tat aca aag acc aca tac tgg tgg gat ggt ctg caa      1347
Gly Gln Arg Lys Tyr Thr Lys Thr Thr Tyr Trp Trp Asp Gly Leu Gln
        430                 435                 440 tca tcc gat gac ttt gct ttg ata gtg aat gcg cct aat cat gaa gga      1395
Ser Ser Asp Asp Phe Ala Leu Ile Val Asn Ala Pro Asn His Glu Gly
        445                 450                 455 ata caa gct gga gta gac aga ttc tat aga act tgc aaa ctg gtc ggg      1443
Ile Gln Ala Gly Val Asp Arg Phe Tyr Arg Thr Cys Lys Leu Val Gly
        460                 465                 470 atc aac atg agc aaa aag aag tcc tac ata aat aga act gga aca ttc      1491
Ile Asn Met Ser Lys Lys Lys Ser Tyr Ile Asn Arg Thr Gly Thr Phe
475                 480                 485                 490 gaa ttc aca agc ttt ttc tac cgg tat ggt ttt gta gcc aat ttc agc      1539
Glu Phe Thr Ser Phe Phe Tyr Arg Tyr Gly Phe Val Ala Asn Phe Ser
                495                 500                 505 atg gaa cta ccc agt ttt ggg gtt tcc gga ata aat gaa tct gca gac      1587
Met Glu Leu Pro Ser Phe Gly Val Ser Gly Ile Asn Glu Ser Ala Asp
        510                 515                 520 atg agc att gga gtg aca gtc atc aaa aac aac atg ata aat aat gat      1635
Met Ser Ile Gly Val Thr Val Ile Lys Asn Asn Met Ile Asn Asn Asp
        525                 530                 535 ctc ggt cct gcc acg gca caa atg gya ctc caa ctc ttc att aag gat      1683
Leu Gly Pro Ala Thr Ala Gln Met Xaa Leu Gln Leu Phe Ile Lys Asp
        540                 545                 550 tat cgg tac aca tac cgg tgc cat aga ggt gat acc cag ata caa acc      1731
Tyr Arg Tyr Thr Tyr Arg Cys His Arg Gly Asp Thr Gln Ile Gln Thr
555                 560                 565                 570 aga aga tct ttt gag ttg aag aaa ctg tgg gaa cag act cga tca aag      1779
Arg Arg Ser Phe Glu Leu Lys Lys Leu Trp Glu Gln Thr Arg Ser Lys
                575                 580                 585 act ggt cta ctg gta tca gat ggg ggt cca aac cta tat aac atc aga      1827
Thr Gly Leu Leu Val Ser Asp Gly Gly Pro Asn Leu Tyr Asn Ile Arg
        590                 595                 600 aac cta cac atc ccg gaa gtc tgt tta aaa tgg gag cta atg gat gaa      1875
Asn Leu His Ile Pro Glu Val Cys Leu Lys Trp Glu Leu Met Asp Glu
        605                 610                 615 gat tat aag ggg agg cta tgc aat cca ttg aat cct ttc gtt agt cac      1923
Asp Tyr Lys Gly Arg Leu Cys Asn Pro Leu Asn Pro Phe Val Ser His
        620                 625                 630 aaa gaa att gaa tca gtc aac agt gca gta gta atg cct gcg cat ggc      1971
Lys Glu Ile Glu Ser Val Asn Ser Ala Val Val Met Pro Ala His Gly
635                 640                 645                 650 cct gcc aaa agc atg gag tat gat gct gtt gca aca aca cat tct tgg      2019
Pro Ala Lys Ser Met Glu Tyr Asp Ala Val Ala Thr Thr His Ser Trp
                655                 660                 665
```

-continued

```
atc ccc aag agg aac cgg tcc ata ttg aac aca agc caa agg gga ata       2067
Ile Pro Lys Arg Asn Arg Ser Ile Leu Asn Thr Ser Gln Arg Gly Ile
        670                 675                 680 cta gaa gat gag cag atg tat cag aaa tgc tgc aac ctg ttt gaa aaa       2115
Leu Glu Asp Glu Gln Met Tyr Gln Lys Cys Cys Asn Leu Phe Glu Lys
685                 690                 695 ttc ttc ccc agc agc tca tac aga aga cca gtc gga att tct agt atg      2163
Phe Phe Pro Ser Ser Ser Tyr Arg Arg Pro Val Gly Ile Ser Ser Met
    700                 705                 710 gtt gag gcc atg gta tcc agg gcc cgc att gat gca cga att gac ttc      2211
Val Glu Ala Met Val Ser Arg Ala Arg Ile Asp Ala Arg Ile Asp Phe
715                 720                 725                 730 gaa tct gga cgg ata aag aag gat gag ttc gct gag atc atg aag atc      2259
Glu Ser Gly Arg Ile Lys Lys Asp Glu Phe Ala Glu Ile Met Lys Ile
                735                 740                 745 tgt tcc acc att gaa gag ctc aga cgg caa aaa tagtgaa                  2299
Cys Ser Thr Ile Glu Glu Leu Arg Arg Gln Lys
                750                 755

<210> SEQ ID NO 14
<211> LENGTH: 757
<212> TYPE: PRT
<213> ORGANISM: Influenza A virus
<220> FEATURE:
<221> NAME/KEY: misc_feature
<222> LOCATION: (547)..(547)
<223> OTHER INFORMATION: The 'Xaa' at location 547 stands for Ala, or
      Val.

<400> SEQUENCE: 14

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ser Asn Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Ile Thr Gln Arg Thr Ile Gly Lys Lys
        195                 200                 205

Lys Gln Arg Leu Ser Arg Lys Ser Tyr Leu Ile Arg Thr Leu Thr Leu
    210                 215                 220
```

```
Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Leu Leu Val Asp Gly Thr
385                 390                 395                 400

Ala Ser Leu Ser Pro Gly Met Met Gly Met Phe Asn Met Leu Ser
                405                 410                 415

Thr Val Leu Gly Val Ser Ile Leu Asn Leu Gly Gln Arg Lys Tyr Thr
                420                 425                 430

Lys Thr Thr Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
        450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Xaa Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Thr Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
    610                 615                 620

Cys Asn Pro Leu Asn Pro Phe Val Ser His Lys Glu Ile Glu Ser Val
625                 630                 635                 640
```

-continued

```
Asn Ser Ala Val Val Met Pro Ala His Gly Pro Ala Lys Ser Met Glu
            645                 650                 655

Tyr Asp Ala Val Ala Thr Thr His Ser Trp Ile Pro Lys Arg Asn Arg
        660                 665                 670

Ser Ile Leu Asn Thr Ser Gln Arg Gly Ile Leu Glu Asp Glu Gln Met
    675                 680                 685

Tyr Gln Lys Cys Cys Asn Leu Phe Glu Lys Phe Phe Pro Ser Ser Ser
690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Asp Glu Phe Ala Glu Ile Met Lys Ile Cys Ser Thr Ile Glu Glu
            740                 745                 750

Leu Arg Arg Gln Lys
        755
```

```
<210> SEQ ID NO 15
<211> LENGTH: 2370
<212> TYPE: DNA
<213> ORGANISM: Influenza A virus
<220> FEATURE:
<221> NAME/KEY: CDS
<222> LOCATION: (42)..(2318)

<400> SEQUENCE: 15
```

```
tattggtctc agggagcgaa agcaggtcaa atatattcaa t atg gag aga ata aaa      56
                                             Met Glu Arg Ile Lys
                                               1               5 gaa ctg aga gat ctg atg tta caa tcc cgc acc cgc gag ata cta aca      104
Glu Leu Arg Asp Leu Met Leu Gln Ser Arg Thr Arg Glu Ile Leu Thr
             10                  15                  20 aaa act act gtg gac cac atg gcc ata atc aag aaa tac aca tca gga      152
Lys Thr Thr Val Asp His Met Ala Ile Ile Lys Lys Tyr Thr Ser Gly
         25                  30                  35 aga caa gag aag aac cct gca ctt agg atg aaa tgg atg atg gca atg      200
Arg Gln Glu Lys Asn Pro Ala Leu Arg Met Lys Trp Met Met Ala Met
     40                  45                  50 aaa tac cca att aca gca gat aag agg ata atg gag atg att cct gag      248
Lys Tyr Pro Ile Thr Ala Asp Lys Arg Ile Met Glu Met Ile Pro Glu
 55                  60                  65 aga aat gaa cag gga caa acc ctt tgg agc aaa acg aac gat gct ggc      296
Arg Asn Glu Gln Gly Gln Thr Leu Trp Ser Lys Thr Asn Asp Ala Gly
 70                  75                  80                  85 tca gac cgc gta atg gta tca cct ctg gca gtg aca tgg tgg aat agg      344
Ser Asp Arg Val Met Val Ser Pro Leu Ala Val Thr Trp Trp Asn Arg
                 90                  95                 100 aat gga cca aca acg aac aca att cat tat ccg aaa gtc tac aaa act      392
Asn Gly Pro Thr Thr Asn Thr Ile His Tyr Pro Lys Val Tyr Lys Thr
             105                 110                 115 tat ttt gaa aag gtt gaa aga ttg aaa cac gga acc ttt ggc ccc gtt      440
Tyr Phe Glu Lys Val Glu Arg Leu Lys His Gly Thr Phe Gly Pro Val
         120                 125                 130 cat ttt agg aat caa gtc aag ata aga cga aga gtt gat gta aac cct      488
His Phe Arg Asn Gln Val Lys Ile Arg Arg Arg Val Asp Val Asn Pro
     135                 140                 145 ggt cac gcg gac ctc agt gct aaa gaa gca caa gat gtg atc atg gaa      536
Gly His Ala Asp Leu Ser Ala Lys Glu Ala Gln Asp Val Ile Met Glu
150                 155                 160                 165
```

-continued

| | | |
|---|---|---|
| gtt gtt ttc cca aat gaa gtg gga gcc aga att cta aca tca gaa tca<br>Val Val Phe Pro Asn Glu Val Gly Ala Arg Ile Leu Thr Ser Glu Ser<br>                170                  175                180 | 584 |
| caa cta aca ata acc aaa gag aaa aag gaa gaa ctt cag gac tgc aaa<br>Gln Leu Thr Ile Thr Lys Glu Lys Lys Glu Glu Leu Gln Asp Cys Lys<br>                185                  190                195 | 632 |
| att gct ccc ttg atg gta gca tac atg cta gaa aga gag ttg gtc cga<br>Ile Ala Pro Leu Met Val Ala Tyr Met Leu Glu Arg Glu Leu Val Arg<br>                200                  205                210 | 680 |
| aaa aca agg ttc ctc cca gta gta ggc gga aca agc agt gta tac att<br>Lys Thr Arg Phe Leu Pro Val Val Gly Gly Thr Ser Ser Val Tyr Ile<br>                215                  220                225 | 728 |
| gaa gtg ttg cat ctg act cag gga aca tgc tgg gag caa atg tac acc<br>Glu Val Leu His Leu Thr Gln Gly Thr Cys Trp Glu Gln Met Tyr Thr<br>230                    235                  240                245 | 776 |
| cca gga gga gaa gtt aga aac gat gat att gat caa agt tta att att<br>Pro Gly Gly Glu Val Arg Asn Asp Asp Ile Asp Gln Ser Leu Ile Ile<br>                  250                  255                260 | 824 |
| gca gcc cgg aac ata gtg aga aga gca aca gta tca gca gat cca cta<br>Ala Ala Arg Asn Ile Val Arg Arg Ala Thr Val Ser Ala Asp Pro Leu<br>                265                  270                275 | 872 |
| gca tcc cta ctg gaa atg tgc cac agt aca cag att ggt gga aca agg<br>Ala Ser Leu Leu Glu Met Cys His Ser Thr Gln Ile Gly Gly Thr Arg<br>                280                  285                290 | 920 |
| atg gta gac atc ctt aag cag aac cca aca gag gaa caa gct gtg gat<br>Met Val Asp Ile Leu Lys Gln Asn Pro Thr Glu Glu Gln Ala Val Asp<br>            295                  300                305 | 968 |
| ata tgc aaa gca gca atg gga ttg aga att agc tca tca ttc agc ttt<br>Ile Cys Lys Ala Ala Met Gly Leu Arg Ile Ser Ser Ser Phe Ser Phe<br>310                    315                  320                325 | 1016 |
| ggt gga ttc acc ttc aaa agg aca agt gga tca tca gtc aag aga gaa<br>Gly Gly Phe Thr Phe Lys Arg Thr Ser Gly Ser Ser Val Lys Arg Glu<br>                330                  335                340 | 1064 |
| gaa gaa atg ctt acg ggc aac ctt caa aca ttg aaa ata aga gtg cat<br>Glu Glu Met Leu Thr Gly Asn Leu Gln Thr Leu Lys Ile Arg Val His<br>                345                  350                355 | 1112 |
| gag ggc tat gaa gaa ttc aca atg gtc gga aga aga gca aca gcc att<br>Glu Gly Tyr Glu Glu Phe Thr Met Val Gly Arg Arg Ala Thr Ala Ile<br>                  360                  365                370 | 1160 |
| atc aga aag gca acc aga aga ttg att caa ttg ata gta agt ggg aga<br>Ile Arg Lys Ala Thr Arg Arg Leu Ile Gln Leu Ile Val Ser Gly Arg<br>            375                  380                385 | 1208 |
| gat gaa caa tca att gct gaa gca ata att gta gcc atg gtg ttt tcg<br>Asp Glu Gln Ser Ile Ala Glu Ala Ile Ile Val Ala Met Val Phe Ser<br>390                    395                  400                405 | 1256 |
| caa gaa gat tgc atg ata aaa gca gtt cga ggc gat ttg aac ttt gtt<br>Gln Glu Asp Cys Met Ile Lys Ala Val Arg Gly Asp Leu Asn Phe Val<br>                410                  415                420 | 1304 |
| aat aga gca aat cag cgt ttg aac ccc atg cat caa ctc ttg agg cat<br>Asn Arg Ala Asn Gln Arg Leu Asn Pro Met His Gln Leu Leu Arg His<br>                425                  430                435 | 1352 |
| ttc caa aaa gat gca aaa gtg ctt ttc caa aat tgg gga att gaa ccc<br>Phe Gln Lys Asp Ala Lys Val Leu Phe Gln Asn Trp Gly Ile Glu Pro<br>                440                  445                450 | 1400 |
| atc gac aat gta atg ggg atg att gga ata ttg cct gac atg acc cca<br>Ile Asp Asn Val Met Gly Met Ile Gly Ile Leu Pro Asp Met Thr Pro<br>            455                  460                465 | 1448 |
| agc acc gag atg tca ttg aga gga gtg aga gtc agc aaa atg gga gtg<br>Ser Thr Glu Met Ser Leu Arg Gly Val Arg Val Ser Lys Met Gly Val<br>470                    475                  480                485 | 1496 |

```
gat gag tac tcc agc act gag aga gtg gtg gtg agc att gac cgt ttt      1544
Asp Glu Tyr Ser Ser Thr Glu Arg Val Val Val Ser Ile Asp Arg Phe
            490                 495                 500 tta aga gtt cgg gat caa agg gga aac ata cta ctg tcc cct gaa gaa      1592
Leu Arg Val Arg Asp Gln Arg Gly Asn Ile Leu Leu Ser Pro Glu Glu
        505                 510                 515 gtc agt gaa aca caa gga acg gaa aag ctg aca ata att tat tcg tca      1640
Val Ser Glu Thr Gln Gly Thr Glu Lys Leu Thr Ile Ile Tyr Ser Ser
    520                 525                 530 tca atg atg tgg gag att aat ggt ccc gaa tca gtg ttg gtc aat act      1688
Ser Met Met Trp Glu Ile Asn Gly Pro Glu Ser Val Leu Val Asn Thr
535                 540                 545 tat caa tgg atc atc aga aac tgg gaa att gta aaa att cag tgg tca      1736
Tyr Gln Trp Ile Ile Arg Asn Trp Glu Ile Val Lys Ile Gln Trp Ser
550                 555                 560                 565 cag gac ccc aca atg tta tac aat aag ata gaa ttt gaa cca ttc caa      1784
Gln Asp Pro Thr Met Leu Tyr Asn Lys Ile Glu Phe Glu Pro Phe Gln
                570                 575                 580 tcc ctg gtc cct agg gcc acc aga agc caa tac agc ggt ttc gta aga      1832
Ser Leu Val Pro Arg Ala Thr Arg Ser Gln Tyr Ser Gly Phe Val Arg
            585                 590                 595 acc ctg ttt cag caa atg cga gat gta ctt gga aca ttt gat act gct      1880
Thr Leu Phe Gln Gln Met Arg Asp Val Leu Gly Thr Phe Asp Thr Ala
        600                 605                 610 caa ata ata aaa ctc ctc cct ttt gcc gct gct cct ccg gaa cag agt      1928
Gln Ile Ile Lys Leu Leu Pro Phe Ala Ala Ala Pro Pro Glu Gln Ser
    615                 620                 625 agg atg cag ttc tct tct ttg act gtt aat gta aga ggt tcg gga atg      1976
Arg Met Gln Phe Ser Ser Leu Thr Val Asn Val Arg Gly Ser Gly Met
630                 635                 640                 645 agg ata ctt gta aga ggc aat tcc ccg gtg ttc aac tac aat aaa gtc      2024
Arg Ile Leu Val Arg Gly Asn Ser Pro Val Phe Asn Tyr Asn Lys Val
                650                 655                 660 act aaa agg ctc aca gtc ctc gga aag gat gca ggt gcg ctt act gag      2072
Thr Lys Arg Leu Thr Val Leu Gly Lys Asp Ala Gly Ala Leu Thr Glu
            665                 670                 675 gac cca gat gaa ggt acg gct gga gta gaa tct gct gtt cta aga ggg      2120
Asp Pro Asp Glu Gly Thr Ala Gly Val Glu Ser Ala Val Leu Arg Gly
        680                 685                 690 ttt ctc att tta ggt aaa gaa aac aag aga tat ggc cca gca cta agc      2168
Phe Leu Ile Leu Gly Lys Glu Asn Lys Arg Tyr Gly Pro Ala Leu Ser
    695                 700                 705 atc aat gaa ctt agc aaa ctt gca aaa ggg gag aaa gcc aat gta cta      2216
Ile Asn Glu Leu Ser Lys Leu Ala Lys Gly Glu Lys Ala Asn Val Leu
710                 715                 720                 725 att ggg caa ggg gac gta gtg ttg gta atg aaa cgg aaa cgt gac tct      2264
Ile Gly Gln Gly Asp Val Val Leu Val Met Lys Arg Lys Arg Asp Ser
                730                 735                 740 agc ata ctt act gac agc cag aca gcg acc aaa agg att cgg atg gcc      2312
Ser Ile Leu Thr Asp Ser Gln Thr Ala Thr Lys Arg Ile Arg Met Ala
            745                 750                 755 atc aat tagtgttgaa ttgtttaaaa acgaccttgt ttctactaat acgagaccat at    2370
Ile Asn <210> SEQ ID NO 16
<211> LENGTH: 759
<212> TYPE: PRT
<213> ORGANISM: Influenza A virus
```

<400> SEQUENCE: 16

```
Met Glu Arg Ile Lys Glu Leu Arg Asp Leu Met Leu Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ala Leu Arg Met Lys
            35                  40                  45

Trp Met Met Ala Met Lys Tyr Pro Ile Thr Ala Asp Lys Arg Ile Met
        50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Asn Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Val Gly Gly Thr
210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Lys Gln Asn Pro Thr Glu
290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Ile Arg Lys Ala Thr Arg Arg Leu Ile Gln Leu
370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415
```

```
Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Ile Leu
            500                 505                 510

Leu Ser Pro Glu Glu Val Ser Glu Thr Gln Gly Thr Glu Lys Leu Thr
        515                 520                 525

Ile Ile Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ile Val
545                 550                 555                 560

Lys Ile Gln Trp Ser Gln Asp Pro Thr Met Leu Tyr Asn Lys Ile Glu
                565                 570                 575

Phe Glu Pro Phe Gln Ser Leu Val Pro Arg Ala Thr Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Val Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asn Lys Arg Tyr
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
            755
```

CANINE INFLUENZA VIRUS AND RELATED COMPOSITIONS AND METHODS OF USE

CROSS-REFERENCE TO RELATED PATENT APPLICATIONS

This patent application claims the benefit of U.S. Provisional Patent Application No. 60/727,808, filed Oct. 18, 2005, the content of which is incorporated herein by reference in its entirety.

TECHNICAL FIELD OF THE INVENTION

The present invention relates to the fields of virology, molecular biology, and immunology. In particular, the present invention relates to canine influenza virus, as well as related compositions and methods of use in inducing an immune response in animals.

BACKGROUND OF THE INVENTION

Influenza virus is an RNA virus belonging to the family Orthomyxoviridae. The viral RNA consists of eight independent segments, which easily recombine among influenza viruses to produce new subtypes.

Nucleoprotein (NP), which is the primary component of the nucleocapsid, is encoded in the fifth segment. The NP and the matrix protein are used to classify the influenza virus into group A, B or C. Since NP is an internal protein, it is not subject to the pressure of selection by a host's immune system. It binds RNA, is part of the transcriptase complex, and is involved in the nuclear-cytoplasmic transport of viral RNA (vRNA).

Neuraminidase (NM), which splits the oc-keto bond that joins a terminal sialic acid and the next sugar residue, thereby allowing the release of viral progeny from infected cells, is encoded by the sixth segment. Nine subtypes (N1-N9) of this enzyme have been identified. All subtypes have two structural regions—a stalk and a head. All N8 proteins have 470 amino acids, the first eight of which are highly conserved. The following region is rich in hydrophobic amino acids and is considered to be the transmembrane domain. The next 51 amino acids make up the stalk region, and the head region begins at Cys91. The last region contains the catalytic site of the enzyme. Cysteine residues in the head and stalk region tend to be highly conserved. There are 6-8 putative N-glycosylation sites.

Hemagglutinin (HA), which is a membrane glycoprotein responsible for the adsorption of the virus into the host cell, is the main antigen to which neutralizing antibodies are directed. Its antigenic variation is the major cause of influenza epidemics. It is encoded by the fourth segment. Sixteen different subtypes (H1-H16) have been identified. HA has a signal peptide of 16 amino acids and two polypeptides (HA1 and HA2) joined by disulfide bridges. HA1 has the amino terminal end, whereas HA2 has the carboxyl terminal end. A hydrophobic region in HA2 anchors HA to the viral membrane. Cysteine residues tend to be highly conserved. There are six putative glycosylation sites, which enable the virus to mask its antigenic sites (Skehel et al., PNAS USA 81: 1779 (1984)).

Other proteins include matrix (M or M1 and M2), nonstructural (NS or NS1 and NS2), PA, PB1, and PB2. The M1 protein is a major component of the virion that binds to the plasma membrane of infected cells by means of two hydrophobic regions at the N-terminus of the protein, whereas M2 is an ion channel and, therefore, an integral membrane protein. The NS1 protein is found in the nucleus and affects cellular RNA transport, splicing, and translation. The NS2 protein is found in the nucleus and cytoplasm and has unknown function. The PA protein is a transcriptase and may have protease activity, whereas the PB 1 protein functions in transcription elongation and the PB2 protein functions in transcription cap binding.

Globally, influenza is the most economically significant respiratory disease in humans, pigs, horses and poultry (Wright et al., Orthomyxoviruses. In: *Fields Virology*. Knipe et al., eds. Lippincott Williams & Wilkins, Philadelphia, 2001. pp. 1533-1579.). Influenza virus is known for its continuous genetic and antigenic changes, which impede effective control of the virus (Wright et al. (2001), supra; Webster et al., Microbiol. Rev. 56: 152-179 (1992)). Of particular concern for prevention of epidemics and pandemics is the emergency of a new subtype of the virus by genetic re-assortment or inter-species transmission (Wright et al. (2001), supra).

Recently, influenza outbreaks have occurred in species, e.g., feline and canine, which historically do not carry influenza virus (Keawcharoen et al., Emerg. Infect. Dis. 10: 2189-2191 (2004); Crawford et al., Science 310: 398-485 (Oct. 21, 2005; published online Sep. 29, 2005); Dubovi et al., Isolation of equine influenza virus from racing greyhounds with fatal hemorrhagic pneumonia. In: *Proceedings of the 47th Annual Meeting of American Association of Veterinary Laboratory Diagnosticians*, Greensboro, N.C., October 2005. p. 158; and Yoon et al., Emerg. Infect. Dis. 11(12): 1974-1976 (December 2005)). Therefore, the host range of influenza virus is expanding.

Outbreaks of respiratory disease in racing greyhounds caused by infection with influenza virus have occurred in Florida in 2004, in eastern and western Iowa in April 2005, and in Texas in 2005. The disease was characterized by rapid onset of fever and cough, rapid respiration, and hemorrhagic nasal discharge. The morbidity was almost 100% in both race track compounds in Iowa, although the mortality was less than 5%. While a large percentage of affected dogs recovered, many succumbed to hemorrhagic pneumonia. Therapeutic administration of broad-spectrum antibiotics reduced the severity of the disease but could not control it.

In view of the above, it is an object of the present invention to provide the influenza virus that infects canines. It is another object of the present invention to provide materials and methods for inducing an immune response to the influenza virus in canines. These and other objects and advantages, as well as additional inventive features, will become apparent from the detailed description provided herein.

BRIEF SUMMARY OF THE INVENTION

The present invention provides an isolated canine influenza virus of subtype H3N8 comprising an HA having SEQ ID NO: 4 or an amino acid sequence that is greater than 99% identical to SEQ ID NO: 4, with the proviso that the amino acids at positions 94 and 233 are identical to SEQ ID NO: 4. In particular, the present invention provides an isolated canine influenza virus of subtype H3N8 deposited with the American Type Culture Collection (Manassas, Va.) on Jun. 29, 2006, as Patent Deposit No. PTA-7694. Accordingly, the present invention also provides a composition comprising attenuated virus as well as a composition comprising inactivated virus.

The present invention also provides isolated or purified proteins. In one embodiment, the present invention provides an isolated or purified HA, which (i) has the amino acid sequence of SEQ ID NO: 4 or (ii) is derived from an influenza virus and which has an amino acid sequence that is greater than 99% identical to SEQ ID NO: 4, with the proviso that the amino acid sequence is identical to that of SEQ ID NO: 4 at amino acid positions 94 and 233, or a fragment of (i) or (ii), wherein the fragment comprises at least nine contiguous amino acids, at least one of which is identical to the amino acid at position 94 or 233 of SEQ ID NO: 4.

In another embodiment, the present invention provides an isolated or purified NM, which (i) comprises the amino acid sequence of SEQ ID NO: 2 or (ii) is derived from an influenza virus and which comprises an amino acid sequence that is greater than 99% identical to SEQ ID NO: 2, with the proviso that the amino acid sequence is identical to that of SEQ ID NO: 2 at amino acid positions 68 and 134, or a fragment of (i) or (ii), wherein the fragment comprises at least nine contiguous amino acids, at least one of which is identical to the amino acid at position 68 or 134 of SEQ ID NO: 2.

In yet another embodiment, the present invention provides an isolated or purified NP, which (i) has the amino acid sequence of SEQ ID NO: 6 or (ii) is derived from an influenza virus and which has an amino acid sequence that is greater than 99% identical to SEQ ID NO: 6, with the proviso that the amino acid sequence is identical to that of SEQ ID NO: 6 at amino acid position 402, or a fragment of (i) or (ii), wherein the fragment comprises at least nine contiguous amino acids, at least one of which is identical to the amino acid at position 402 of SEQ ID NO: 6.

In still yet another embodiment, the present invention provides an isolated or purified M1, which (i) has the amino acid sequence of SEQ ID NO: 8 or (ii) is derived from an influenza virus and which has an amino acid sequence that is greater than 99% identical to SEQ ID NO: 8, with the proviso that the amino acid sequence is identical to that of SEQ ID NO: 8 at amino acid position 111, or a fragment of (i) or (ii), wherein the fragment comprises at least nine contiguous amino acids, at least one of which is identical to the amino acid at position 111 of SEQ ID NO: 8.

Also provided is an isolated or purified NS1, which has the amino acid sequence of SEQ ID NO: 10.

Further provided is an isolated or purified PA protein, which (i) has the amino acid sequence of SEQ ID NO: 12 or (ii) is derived from an influenza virus and which has an amino acid sequence that is greater than 98% (or 99%) identical to SEQ ID NO: 12, with the proviso that the amino acid sequence is identical to that of SEQ ID NO: 12 at amino acid positions 233, 256, 327, and 561, or a fragment of (i) or (ii), wherein the fragment comprises at least nine contiguous amino acids, at least one of which is identical to the amino acid at position 233, 256, 327, and 561, of SEQ ID NO: 12.

Still further provided is an isolated or purified PB 1, which (i) has the amino acid sequence of SEQ ID NO: 14 or (ii) is derived from an influenza virus and which has an amino acid sequence that is greater than 99% identical to SEQ ID NO: 14, with the proviso that the amino acid sequence is identical to that of SEQ ID NO: 14 at amino acid positions 200 and 213, or a fragment of (i) or (ii), wherein the fragment comprises at least nine contiguous amino acids, at least one of which is identical to the amino acid at position 200 or 213 of SEQ ID NO: 14.

Even still further provided is an isolated or purified PB2, which (i) has the amino acid sequence of SEQ ID NO: 16 or (ii) is derived from an influenza virus and which has an amino acid sequence that is greater than 99% identical to SEQ ID NO: 16, with the proviso that the amino acid sequence is identical to that of SEQ ID NO: 16 at amino acid positions 107, 221, 292, and 661, or a fragment of (i) or (ii), wherein the fragment comprises at least nine contiguous amino acids, at least one of which is identical to the amino acid at position 107, 221, 292, or 661 of SEQ ID NO: 16.

In view of the above, the present invention further provides a composition comprising an above-described protein, such as HA or NM, or a fragment thereof in an amount sufficient to induce an immune response in an animal and a biologically acceptable carrier.

Also in view of the above, the present invention provides a method of inducing an immune response to canine influenza virus in an animal. The method comprises administering to the animal the composition comprising a protein or fragment thereof.

An isolated or purified nucleic acid encoding above-described protein or fragment thereof, optionally as part of a vector, is also provided, as is a composition comprising the isolated or purified nucleic acid, which expresses the protein, such as HA or NM, or a fragment thereof, in an amount sufficient to induce an immune response in an animal and a biologically acceptable carrier.

Accordingly, the present invention also provides another method of inducing an immune response to canine influenza virus in an animal. The method comprises administering to the animal the composition comprising a nucleic acid.

BRIEF DESCRIPTION OF THE FIGURES

FIG. 1 is the partial nucleotide sequence (SEQ ID NO: 1; see also GenBank Acc. No. DQ146420) of the coding domain sequence (CDS) of the NM gene from subtype H3N8 of canine influenza virus. In accordance with convention, the sequence is presented from left to right and top to bottom.

FIG. 2 is the amino acid sequence (SEQ ID NO: 2; see also GenBank Acc. No. DQ146420) encoded by SEQ ID NO: 1. In accordance with convention the sequence is presented in single letter format from left to right and top to bottom.

FIG. 3 is the complete nucleotide sequence (SEQ ID NO: 3; see also GenBank Acc. No. DQ146419) of the CDS of the HA gene from subtype H3N8 of canine influenza virus.

FIG. 4 is the amino acid sequence (SEQ ID NO: 4; see also GenBank Acc. No. DQ146419) encoded by SEQ ID NO: 3.

FIG. 5 is the complete nucleotide sequence (SEQ ID NO: 5) of the CDS of the gene from subtype H3N8 of canine influenza virus.

FIG. 6 is the deduced amino acid sequence (SEQ ID NO: 6) encoded by SEQ ID NO: 5.

FIG. 7 is the complete nucleotide sequence (SEQ ID NO: 7) of the CDS of the M1 protein gene from subtype H3N8 of canine influenza virus.

FIG. 8 is the deduced amino acid sequence (SEQ ID NO: 8) encoded by SEQ ID NO: 7.

FIG. 9 is the complete nucleotide sequence (SEQ ID NO: 9) of the CDS of the NS1 protein gene from subtype H3N8 of canine influenza virus.

FIG. 10 is the deduced amino acid sequence (SEQ ID NO: 10) encoded by SEQ ID NO: 9.

FIG. 11 is the complete nucleotide sequence (SEQ ID NO: 11) of the CDS of the PA protein gene from subtype H3N8 of canine influenza virus.

FIG. 12 is the deduced amino acid sequence (SEQ ID NO: 12) encoded by SEQ ID NO: 11.

FIG. 13 is the complete nucleotide sequence (SEQ ID NO: 13) of the CDS of the PB1 protein gene from subtype H3N8 of canine influenza virus.

FIG. 14 is the deduced amino acid sequence (SEQ ID NO: 14) encoded by SEQ ID NO: 13.

FIG. 15 is the complete nucleotide sequence (SEQ ID NO: 15) of the CDS of the PB2 protein gene from subtype H3N8 of canine influenza virus.

FIG. 16 is the deduced amino acid sequence (SEQ ID NO: 16) encoded by SEQ ID NO: 15.

DETAILED DESCRIPTION OF THE INVENTION

The present invention is predicated on the discovery of a strain of influenza virus in canines. The strain was isolated from racing greyhounds in eastern and western Iowa. The strain has been classified as an H3N8 subtype, and has been designated A/canine/Iowa/13628/2005. Accordingly, the present invention provides a virus comprising an HA having SEQ ID NO: 4 or an amino acid sequence that is greater than 99% identical to SEQ ID NO: 4, with the proviso that the amino acids at positions 94 and 233 are identical to SEQ ID NO: 4. The virus can further comprise an NM comprising the amino acid sequence of SEQ ID NO: 2 or an amino acid sequence that is greater than 99% identical to SEQ ID NO: 2, with the proviso that the amino acids at positions 68 and 134 are identical to SEQ ID NO: 2. The virus comprising the aforementioned HA, alone or in further combination with the aforementioned NM, can further comprise at least one of the following: an NP having the amino acid sequence of SEQ ID NO: 6 or an amino acid sequence that is greater than 99% identical to SEQ ID NO: 6, with the proviso that amino acid 402 is identical to that of SEQ ID NO: 6; an M1 having the amino acid sequence of SEQ ID NO: 8 or an amino acid sequence that is greater than 99% identical to SEQ ID NO: 8, with the proviso that amino acid 111 is identical to that of SEQ ID NO: 8; an NS1 having the amino acid sequence of SEQ ID NO: 10; a PA protein having the amino acid sequence of SEQ ID NO: 12 or an amino acid sequence that is greater than 98% (or 99%) identical to SEQ ID NO: 12, with the proviso that amino acids 233, 256, 327, and 561 are identical to SEQ ID NO: 12; a PB1 having the amino acid sequence of SEQ ID NO: 14 or an amino acid sequence that is greater than 99% identical to SEQ ID NO: 14, with the proviso that amino acids 200 and 213 are identical to SEQ ID NO: 14; and/or PB2 having the amino acid sequence of SEQ ID NO: 16 or an amino acid sequence that is greater than 99% identical to SEQ ID NO: 16, with the proviso that amino acids 107, 221, 292, and 661 are identical to SEQ ID NO: 16. In particular, the present invention provides an isolated canine influenza virus of subtype H3N8 deposited with the American Type Culture Collection, 10801 University Blvd., Manassas, Va. 20110-2209, U.S.A., on Jun. 29, 2006, as Patent Deposit No. PTA-7694.

Influenza virus can be precipitated by subjecting the virus in aqueous medium to one or more insolubilizing steps brought about by the presence of up to 5% by weight of polyethylene glycol (PEG) having a molecular weight between 3,000 and 20,000 or another linear filamentary non-charged polymer in an amount equivalent to the solubilizing power of PEG, separating an insolublized fraction from a non-insolubilized fraction, and recovering virus from one of the fractions (see, e.g., U.S. Pat. No. 3,989,818). Preferably, the temperature does not exceed 35° C., the pH is between 6 and 9, and the ionic strength of the aqueous medium is below the salting out point for the virus. The concentration of the virus in the aqueous medium prior to insolubilizing corresponds to a hemagglutination titer of at least 1 in 32. Aggregated viral particles are obtained, which are believed to provide a better antigenic effect due to the slow release of viral particles after vaccination. If, however, non-aggregated or less aggregated particles are desired, they can be dissociated using any suitable method, such as sonication.

The virus can be attenuated by passaging in a cell system until the virus has lost its ability to produce disease, while fully retaining its immungenic character. For example, the virus can be serially passaged in a culture of cells originating from a canine species or other suitable species at a temperature of about 37 ° C. At each passage, the virus is harvested from one culture and inoculated into a medium containing a fresh cell culture in accordance with methods known in the art. For example, the virus can be collected from tissue cell culture fluids and/or cells. Optionally, during harvesting, the cell culture can be sonicated to promote release of the virus. See, e.g., U.S. Pat. Nos. 5,698,433 and 6,455,298.

If desired, an influenza strain can be passaged at least once in the allantoic cavity of embryonated eggs, such as chicken eggs, in the presence of serum, to obtain serum-resistant virus (see, e.g., U.S. Pat. No. 3,953,592; Kilbourne et al., J. Exp. Med. 111: 387 (1960); Kilbourne, Science 160: 74-75 (April 1968); and Laver et al., Virology 30: 493-501 (1966)). High potency influenza vaccine with low pyrogenicity and low endotoxicity can be achieved by treating the concentrated allantoic fluid containing an attenuated virus sequentially with butyl acetate and ethyl acetate, followed by flash evaporation (see, e.g., U.S. Pat. No. 4,000,257). Such virus can be administered intranasally as a vaccine.

Once inoculated into the host, the virus multiplies to some extent so that only a small initial inoculum is required. The virus must be innocuous, and infection of susceptible contacts should be kept to a minimum.

Alternatively, the virus can be inactivated by abolishing replication and virulence. This can be done by chemical or physical means. Chemical inactivation can be carried out by treatment of the virus with an enzyme, formaldehyde, β-propiolacton or derivative thereof, ethyleneimine or derivative thereof, an organic solvent (e.g., halogenated hydrocarbon), and/or a detergent (e.g., Tween®, Triton X®, sodium desoxycholate, sulfobetain, or cetyltrimethylammonium salts). If necessary, chemically activated compositions can be neutralized. For example, if formaldehyde is used to deactivate the composition, the composition can be neutralized with thiosulphate. If required, the pH subsequently can be returned to a value of about 7. Alternatively, the virus can be extracted with a mixture of ether and ethanol, the aqueous and organic phases can be separated, and residual ether can be removed from the viral suspension under reduced pressure (see, e.g., U.S. Pat. No. 4,431,633). Physical inactivation advantageously can be carried by subjecting the virus to energy-rich radiation, such as ultraviolet light, γ-radiation, or X-rays. Inactivated forms require a relatively high amount of inoculum and, therefore, a correspondingly large quantity of antigenic material, which has to be manufactured, tested, and distributed.

In view of the above, the present invention also provides a composition comprising an attenuated or inactivated virus. The virus should be present in an amount sufficient to induce an immune response and, desirably, should provide protection upon challenge. Generally, an adjuvant, such as Tween®, Span®, Freund's complete adjuvant, saponin, *Corynebacterium parvum* (Coparvax®), aluminium phosphate, aluminium hydroxide, or a mixture thereof, is added to the composition, particularly if the composition comprises inactivated virus. Protein hydrolysates and/or amino acids can be added to stabilize the composition (see, e.g., U.S. Pat. No. 4,537,769). Alternatively, the composition can be formulated as an oil-in-water emulsion using oils such as Marcol and/or Arlacel.

Recombinant influenza strains also can be prepared, such as from the combination of an "over-attenuated" (i.e., the number of passages for attenuation is substantially greater than what is normally required to remove pathogenicity) influenza A parent strain, e.g., A2, with a virulent influenza strain as provided herein (see, e.g., U.S. Pat. No. 3,991,179; also, see U.S. Pat. Nos. 4,009,258; 4,278,662; 4,318,903; 4,338,296; and 4,693,893). A recombinant strain preferably has the growth characteristics of the over-attenuated strain coupled with the antigenic properties, e.g., the HA and NM proteins, of the virulent strain. The selection of strains of influenza virus for vaccine formulation is described in U.S. Pat. No. 5,162,112. Recombinant strains can be formulated as compositions for inducing an immune response.

Sucrose, arginine monohydrochloride, the monosodium monohydrate of glutamic acid, and gelatin hydrolysate can be used to stabilize an influenza virus composition for storage in a refrigerator. See, e.g., U.S. Pat. App. Pub. No. 2006/0110406.

In view of the above, the present invention also provides an isolated or purified HA. The HA either has the amino acid sequence of SEQ ID NO: 4 or is derived from an influenza virus and has an amino acid sequence that is greater than 99% identical to SEQ ID NO: 4, with the proviso that the amino acid sequence is identical to that of SEQ ID NO: 4 at amino acid positions 94 and 233. A fragment of HA comprising at least nine (such as 9, 12, 15, 18, 21 or 24) contiguous amino acids, at least one of which is identical to the amino acid at position 94 or 233 of SEQ ID NO: 4, is also provided.

An isolated or purified NM is also provided. The NM comprises the amino acid sequence of SEQ ID NO: 2 or is derived from an influenza virus and comprises an amino acid sequence that is greater than 99% identical to SEQ ID NO: 2, with the proviso that the amino acid sequence is identical to that of SEQ ID NO: 2 at amino acid positions 68 and 134. A fragment of NM comprising at least nine contiguous amino acids, at least one of which is identical to the amino acid at position 68 or 134 of SEQ ID NO: 2, is also provided.

Further provided is an isolated or purified NP. The NP has the amino acid sequence of SEQ ID NO: 6 or is derived from an influenza virus and has an amino acid sequence that is greater than 99% identical to SEQ ID NO: 6, with the proviso that the amino acid sequence is identical to that of SEQ ID NO: 6 at amino acid position 402. A fragment of NP comprising at least nine contiguous amino acids, at least one of which is identical to the amino acid at position 402 of SEQ ID NO: 6, is also provided.

Still further provided is an isolated or purified M1. The M1 has the amino acid sequence of SEQ ID NO: 8 or is derived from an influenza virus and has an amino acid sequence that is greater than 99% identical to SEQ ID NO: 8, with the proviso that the amino acid sequence is identical to that of SEQ ID NO: 8 at amino acid position 111. A fragment of M1 comprising at least nine contiguous amino acids, at least one of which is identical to the amino acid at position 111 of SEQ ID NO: 8, is also provided.

Even still further provided is an isolated or purified NS1, which has the amino acid sequence of SEQ ID NO: 10.

An isolated or purified PA protein is also provided. The PA has the amino acid sequence of SEQ ID NO: 12 or is derived from an influenza virus and has an amino acid sequence that is greater than 98% (or 99%) identical to SEQ ID NO: 12, with the proviso that the amino acid sequence is identical to that of SEQ ID NO: 12 at amino acid positions 233, 256, 327, and 561. A fragment of PA comprising at least nine contiguous amino acids, at least one of which is identical to the amino acid at position 233, 256, 327, or 561 of SEQ ID NO: 12, is also provided.

An isolated or purified PB1 is provided. The PB1 has the amino acid sequence of SEQ ID NO: 14 or is derived from an influenza virus and has an amino acid sequence that is greater than 99% identical to SEQ ID NO: 14, with the proviso that the amino acid sequence is identical to that of SEQ ID NO: 14 at amino acid positions 200 and 213. A fragment of PB1 comprising at least nine contiguous amino acids, at least one of which is identical to the amino acid at position 200 or 213 of SEQ ID NO: 14, is also provided.

Provided also is an isolated or purified PB2. The PB2 has the amino acid sequence of SEQ ID NO: 16 or is derived from an influenza virus and has an amino acid sequence that is greater than 99% identical to SEQ ID NO: 16, with the proviso that the amino acid sequence is identical to that of SEQ ID NO: 16 at amino acid positions 107, 221, 292, and 661. A fragment of PB2 comprising at least nine contiguous amino acids, at least one of which is identical to the amino acid at position 107, 221, 292, or 661 of SEQ ID NO: 16, is provided as well.

The above proteins and fragments thereof can be purified (coupled with chemical or physical fragmentation to generate fragments) or synthesized in accordance with methods known in the art. See, e.g., Meienhofer, Hormonal Proteins and Peptides 2: 46, Academic Press, NY (1973), for solid phase protein synthesis, and Schroder et al., The Peptides, vol. 1, Academic Press, NY (1965), for solution phase protein synthesis. Automated systems can be used to carry out such techniques in accordance with manufacturer's instructions. Therapeutic quantities can be recombinantly produced and purified.

Alternatively, proteins, in particular HA and NM, can be isolated by selective solubilization, while leaving residual subviral particles consisting of the intact lipid/protein membrane enclosing all other non-essential viral components. The difference in size/density of the solubilized proteins and the residual subviral particles allows separation based on differences in physical properties by gradient centrifugation and fractionation, sedimentation, molecular sieve chromatography, or pelleting in an ultracentrifuge. Selective solubilization of HA and NM can be achieved by treatment of the virus with a cationic detergent (see, e.g., U.S. Pat. No. 4,140,762; the '762 patent). The whole virus-containing fluid obtained from cell culture can be treated with a DNA-digesting enzyme followed by addition of a cationic detergent and isolation of surface-antigen proteins (see, e.g., U.S. Pat. No. 5,948,410). The fluid can be subjected to several ultracentrifugation steps, or the virus can be fragmented in the presence of an amphiphilic nonionic detergent followed by filtration to remove undesirable substances (see, e.g., U.S. Pat. No. 6,048,537). Alternatively, membrane filtration and chemical splitting can be used to obtain a viral protein (see, e.g., U.S. Pat. No. 4,327,182). Other procedures are described in U.S. Pat. Nos. 4,064,232 and 4,057,626. Preferably, the virus is multiplied before treatment as exemplified in the '762 patent (col. 2, 11. 10 et seq).

Mapping can be conducted to identify an immune response-inducing epitope of a viral protein, i.e., "epitope mapping." Such mapping involves fragmenting of a protein into overlapping peptides (such as peptides comprising 9, 12, 15, 18, 21 or 24 amino acids). The protein can be fragmented with a proteolytic enzyme. The individual peptides are then tested for their ability to bind to an antibody elicited by the native protein or to induce T-cell or B-cell activation. Alternatively, hydrophilic regions of the protein can be selected, since hydrophilic residues are often on the surface of the protein and, therefore, are accessible to the antibody. X-ray crystallographic analysis of the antigen-antibody complex also can be performed. Potential HLA anchor binding motifs, which are peptide sequences that are known to be likely to bind to MHC molecules, can be identified from the amino acid sequence of a protein. Preferably, the epitope selected is one that shares little to no sequence identity with sequences widely found in the animal to which a composition comprising or expressing a protein fragment will be administered.

An isolated or purified nucleic acid encoding an above-described protein or fragment thereof, optionally as part of a vector, is also provided. The nucleic acid encoding the HA can comprise the nucleotide sequence of SEQ ID NO: 3 or a fragment thereof encoding at least nine (9, 12, 15, 18, 21 or 24) contiguous amino acids. If desired, a trivalent vaccine based on HA can be prepared, wherein one of the HAs comprises the amino acid sequence of SEQ ID NO: 4 (see, e.g., U.S. Pat. Nos. 5,762,939 and 6,245,532; see, e.g., U.S. Pat. No. 6,740,325 for a tetravalent vaccine). The nucleic acid encoding the NM can have the nucleotide sequence of SEQ ID NO: 1 or a fragment thereof encoding at least nine contiguous amino acids (see, e.g., U.S. Pat. No. 6,605,457 and U.S. Pat. App. Pub. No. 2003/0129197), whereas the nucleic acid encoding the NP can have the nucleotide sequence of SEQ ID NO: 5 or a fragment thereof encoding at least nine contiguous amino acids, the nucleic acid encoding the M1 protein can have the nucleotide sequence of SEQ ID NO: 7 or a fragment thereof encoding at least nine contiguous amino acids, the nucleic acid encoding the NS1 protein can have the nucleotide sequence of SEQ ID NO: 9, the nucleic acid encoding the PA can have the nucleotide sequence of SEQ ID NO: 11 or a fragment thereof encoding at least nine contiguous amino acids, the nucleic acid encoding the PB1 can have the nucleotide sequence of SEQ ID NO: 13 or a fragment thereof encoding at least nine contiguous amino acids, and the nucleic acid encoding the PB2 can have the nucleotide sequence of SEQ ID NO: 15 or a fragment thereof encoding at least nine contiguous amino acids. One of ordinary skill in the art will appreciate, however, that due to the degeneracy of the genetic code, there are numerous other nucleotide sequences that can encode such amino acid sequences.

The above nucleic acids, which can be DNA or RNA, and fragments thereof can be synthesized (see, e.g., Oligonucleotide Synthesis, Gait, ed., 1984). Such molecules can include non-naturally occurring nucleotides/bases that encode the desired amino acid sequence. For example, the base or sugar can be methylated. In addition, the backbone of the nucleic acid molecule can be modified, e.g., a phosphorothioate backbone, methylphosphonate, methylphosphorothioate, phosphorodithioate, and combinations thereof.

Alternatively, isolated vRNA can be subjected to reverse transcriptase to produce an RNA/DNA hybrid, from which the RNA is digested away and the residual DNA is treated to produce a dsDNA having a hairpin end, which is treated with a single-strand-specific nuclease to produce a bimolecular double-stranded copy of the vRNA (see, e.g., U.S. Pat. No. 4,357,421). See, e.g., U.S. Pat. App. Pub. No. 2006/0166321 for the use of tandem transcription cassettes for the preparation of influenza in the absence of helper virus.

The nucleic acid is optionally part of a DNA vector comprising at least one promoter, in which case each nucleotide sequence is operably linked to a promoter, which can be the same or different. In addition to promoters, other control sequences, such as terminating signals and the like, can be part of the DNA vector.

For example, the nucleic acid can be introduced into a suitable recombinant expression vector, such as those adapted for bacteria, such as *E. coli* and *Salmonella typhi*, yeast, such as *Saccharomyces cervisiae* or *Pichia pastoris*, or filamentous fungi, such as *Aspergillus nidulans*. The bacteria, yeast, or fungi can be grown in continuous culture. The polypeptide, which is produced during culture, then can be isolated and purified. Alternatively, the nucleic acid molecule can be introduced into Poxviridae (e.g., fowlpox-based vectors), Herpesviridae (e.g., pseudorabies virus-based vectors, turkey herpes virus-based vectors, feline herpes virus-based vectors, infectious laryngotracheitis virus-based vectors, and bovine herpes virus-based vectors), Adenoviridae (e.g., bovine adenovirus (e.g., serotype 3), human adenovirus (e.g., serotype 4 or 7), and canine adenovirus (e.g., serotype 2; CAV2; see, e.g., U.S. Pat. No. 6,090,393), or an insect virus expression vector, such as recombinant baculovirus (e.g., *Autographa californica* nuclear polyhydrosis virus (AcNPV)), which, in turn, can be used to infect susceptible cultured SF9 cells, which are derived from the insect *Spodotera frugiperda*. Other viral vectors include vaccinia (see, e.g., U.S. Pat. No. 4,722,848), adenovirus, adeno-like virus, adeno-associated virus, retrovirus, and pox (see, e.g., Hruby, Vet. Parasitol. 29: 281-282 (1988); Uiu, "AIDS Research Reviews," Dekker, Inc., 1991, 1: 403-416), which can be administered by a skin scratch or by injection, optionally as a liposomal formulation. Other vectors include Bacille-Calmette-Guerin (BCG; Stover et al., Nature 351: 456-460 (1991)), detoxified anthrax toxin vectors, and the like. Mammalian cells, such as Chinese hamster ovary (CHO) cells, and even plant cells can be used to express the polypeptide from the appropriate construct. One of ordinary skill in the art will appreciate that the choice of host cell will affect the nature of post-translational processing (e.g., glycosylation, folding, and the like), which, in turn, can impact the immunogenicity of the polypeptide, and subsequent purification techniques.

Expression can be achieved in any appropriate host cell transformed/transfected with the expression vector. Examples of suitable host cells include, but are not limited to, those described above. Thus, the present invention also provides a host cell transformed/transfected with an expression vector.

Supernatants from host/vector systems that secrete the protein or fragment thereof into culture media can be applied to a purification matrix, such as an affinity column or an ion exchange column. One or more reverse-phase HPLC steps can be employed to purify further the recombinant protein or fragment thereof.

Production of a protein or fragment thereof as a fusion protein can stabilize production. This can be accomplished by ligating polynucleotide sequences encoding two or more proteins (or fragments thereof) into an appropriate expression vector with or without a peptidic linker. Desirably, the reading frames of the polynucleotides sequences are in phase, so that a single fusion protein that retains the biological activity of each protein (or fragment thereof) is produced. A peptidic linker from 1 to about 50 amino acids can be used to separate the resultant proteins (or fragments thereof) so as to ensure that each protein (or fragment thereof) properly folds into its native secondary, tertiary, and quaternary structures (see, e.g., Maratea et al., Gene 49: 39-46 (1985); Murphy et al., PNAS USA 83: 8258-8262 (1986); U.S. Pat. Nos. 4,935,233; and 4,751,180). The ability to adopt a flexible extended conformation, the inability to adopt a secondary structure that could interact with functional amino acids on either one or both of the proteins, and the lack of hydrophobic or charged residues that might react with either one or both of the proteins are factors, which are taken into consideration in selecting a peptide linker. Linkers are not required when the ends of the proteins to be joined do not contain essential regions, such that the ends can be used to separate functional domains and prevent steric interference. Preferred peptide linker sequences contain Gly, Asn, and Ser residues. Other near neutral residues, such as Thr and Ala, also can be used.

Other additional amino acid sequence(s) can be selected to enhance the expression and/or immunogenicity of the protein or fragment thereof. For example, the protein or fragment thereof can be fused to the heavy chain of immunoglobulin G (IgG) or an antigen-presenting cell (APC) binding protein or a dendritic cell binding protein, such as IL-D, GM-CSF, IL-1, TNF, IL-4, CD40L, CTLA4, CD28, or FLT-3 ligand. Techniques, such as the use of dehydrating agents, e.g., dicyclohexylcarbodiimide (DCCI), or the creation of linkages between sulfhydryl groups, epsilon amino groups, carboxyl groups, and the like, can be used. If desired, a cleavage site can be introduced into the fusion protein to enable separation of the protein (or fragment thereof) from the non-naturally occurring sequence(s). Examples of cleavage sites include a target sequence for a proteolytic enzyme or, if methionine is not present in the protein (or fragment thereof), methionine, which, in turn, is cleaved by cyanogen bromide. Such methods are known in the art. The protein or fragment thereof can be modified by glycosylation or other derivatization (e.g., acetylation or carboxylation), also in accordance with methods known in the art.

The protein (or fragment thereof) can be expressed in situ from a suitable expression system. Any DNA construct, which is effective in producing the encoded protein or fragment thereof in the desired environment, can be used to express the protein or fragment thereof as described above.

Alternatively, the nucleic acid molecule can behave as an effective expression system in situ when injected into an animal as "naked DNA" (see, e.g., Ulmer et al., Science 259: 1745-1749 (1993); and Cohen, Science 259: 1691-1692 (1993)). DNA delivery also can be facilitated through the use of bupivicaine, polymers, and peptides; alternatively, cationic lipid complexes, particles, or pressure (see, e.g., U.S. Pat. No. 5,922,687) can be used.

Examples of amino acid sequences that are at least about or greater than 95% identical to, such as at least about or greater than 96%, 97%, 98%, or 99% identical to, SEQ ID NO: 2, 4, 6, 8, 10, 12, 14, or 16 include amino acid sequences that contain one or more substitutions, insertions, additions and/or deletions. Sequence identity can be determined by aligning polypeptide sequences and applying publicly available computer algorithms, such as BLASTP (Pearson et al., PNAS USA 85: 2444-2448 (1988); Pearson, Methods Enzymol. 183: 63-98 (1990); and Altschul et al., Nucl. Acids Res. 25: 3389-3402 (1997)). The software for BLASTP is available on the FTP server of the National Center for Biotechnology Information (NCBI) or NCBI, National Library of Medicine, Building 38A, Room 8N805, Bethesda, M.d 20894. Once the polypeptide sequences are aligned, the number of identical amino acids over the aligned portions is identified, the number of identical amino acids is divided by the total number of amino acids of the polypeptide of interest, and the result is multiplied by 100 to determine the percentage sequence identity.

In this regard, one of ordinary skill in the art will appreciate that a fragment of a given amino acid sequence can be at least about or greater than 95% identical to, such as 96%, 97%, 98% or 99% identical to, the amino acid sequence. Thus, fragments are intended to be encompassed by "an amino acid sequence that is at least about or greater than 95% (or 96%, 97%, 98% or 99%) identical to SEQ ID NO: 2, 4, 6, 8, 10, 12, 14, or 16." Such fragments desirably retain the immunogenicity of the full-length protein. Functional fragments can be generated by mutational analysis of the nucleic acid encoding the protein and subsequent expression of the resulting mutant protein or by chemical/enzymatic digestion of the protein, itself.

Modifications, such as substitutions, insertions, additions and/or deletions, can be introduced into the nucleic acid or the protein (or fragment thereof) in accordance with methods known in the art (see, e.g., Adelman et al., DNA 2: 183 (1983), for oligonucleotide-directed site-specific mutagenesis). Desirably, the modification does not substantially diminish the immunogenicity of the protein fragment; rather, it is preferred that the immunogenicity remains substantially the same or increases relative to the unmodified protein.

A "conservative substitution" is one in which an amino acid is substituted for another amino acid that has similar properties, i.e., similar secondary structure and hydropathic nature. Amino acid substitutions can be made on the basis of similarity in polarity, charge, solubility, hydrophobicity, hydrophilicity and/or the amphipathic nature of the residues. For example, negatively charged amino acids, such as aspartic acid and glutamic acid, can be interchanged, whereas positively charged amino acids, such as lysine and arginine, can be interchanged, and amino acids with uncharged polar head groups having similar hydrophilicity values can be interchanged. In this regard, leucine, isoleucine and valine can be interchanged, glycine and alanine can be interchanged, asparagine and glutamine can be interchanged, and serine, threonine, phenylalanine, and tyrosine can be interchanged. Other groups of amino acids that can be interchanged include: (1) ala, pro, gly, glu, asp, gln, asn, ser and thr; (2) cys, ser, tyr and thr; (3) val, ile, leu, met, ala and phe; (4) lys, arg and his; and (5) phe, tyr, tip, and his.

In view of the above, a composition comprising the isolated or purified protein/nucleic acid or fragment of either of the foregoing and a biologically acceptable carrier is also provided. The nucleic acid or fragment thereof can be part of a vector. See, for example, U.S. Pat. No. 4,029,763, which is directed to an influenza vaccine comprising, as an active ingredient, NM, and U.S. Pat. No. 4,140,762, which is directed to an influenza vaccine comprising, as active ingredients, HA and NM. U.S. Pat. No. 4,826,687 describes the addition of muramyl dipeptide to a vaccine comprising HA and NM. If desired, polypeptides corresponding substantially to amino acids 148-162, 163-166, and/or 215-239 of M1 can be added to a composition of a protein/nucleic acid or fragment thereof (see, e.g., U.S. Pat. Nos. 5,136,019; 5,616,327; and 5,741,493). Any suitable biologically acceptable carrier can be used in the composition. For example, the protein(s)/nucleic acid(s)/fragments thereof can be resuspended in a diluent, e.g., 0.9% sodium chloride solution, which is optionally buffered with, for example, a phosphate buffer. Any sucrose that remains from purification of the virus can be reduced by dialysis. Dialysis or gel chromatography can be used to remove any remaining cationic detergent. Preferably, the protein or fragment thereof is present in an amount sufficient to induce an immune response (i.e., cellular or humoral) in an animal. A frequently selected carrier for pharmaceuticals and antigens is poly(d,l-lactide-co-glycolide) (PLGA). PLGA is a biodegradable polyester, and can be used for the controlled release of antigen (Eldridge et al., Curr. Topics Micro. Immuno. 146: 59-66 (1989); see also U.S. Pat. No. 6,090,393). The entrapment of antigens in PLGA microspheres of 1-10 µ in diameter has been shown to have a remarkable adjuvant effect when administered orally.

If desired, a preserving agent or an inactivating agent, such as formaldehyde, can be added. A conventional amount of preserving/inactivating agent is 1 part per 10,000 parts.

If desired, one or more proteins (or immunogenic fragments thereof), such as the above-described HA, can be combined with proteosomes. See, e.g., U.S. Pat. No. 6,743,900 and U.S. Pat. App. Pub. No. 2004/0156867.

Immunogenicity can be improved by inclusion of conventional immunological adjuvants, such as aluminium hydroxide (e.g., about 0.2%) or aluminium phosphate, aluminum (see, e.g., U.S. Pat. Nos. 6,372,223, 6,635,246, 6,861,244 and 7,052,701 and U.S. Pat. App. Pub. Nos. 2004/0096464 and 2006/0147468), chitosan (see, e.g., U.S. Pat. Nos. 6,136,606 and 6,534,065), alum, such as in the form of aluminum hydroxide, aluminum phosphate or aluminum oxide, mineral oils (e.g., Bayol F® and Marcol 52®), Freund's complete adjuvant, Freund's incomplete adjuvant, muramyl dipeptide, monophosphoryl lipid A, and saponins, including the Quil A component. Immunogenicity also can be improved by adding a cytokine, such as an interleukin, or by conjugating proteins or fragments thereof. Preferably, the protein or fragment thereof is conjugated with a macromolecular carrier, such as a protein (e.g., serum albumin, keyhole limpet hemocyanin, imunoglobulin, throglobulin, and ovalbumin), polysaccharide (e.g., latex-functionalized sepharose, agarose, cellulose beads, and the like), phospholipid, polymeric amino acids (e.g., polyglutamic acid, polylysine, and the like), or amino acid co-polymers (see, e.g., U.S. Pat. Nos. 5,136,019 and 5,612,037). Alternatively, the protein or fragment thereof can be encapsulated with a proteoliposome or lipid vesicle.

The composition, which can induce an immune response, can be prepared in the form of a suspension or can be lyophilized. If lyophilized, it is preferable to add one or more stabilizers. Suitable stabilizers are, for example, sucrose, phosphate, glutamate, and albumin (SPGA; Bovarnick, J. Bacteriol. 59: 509 (1950)), carbohydrates (e.g., sorbitol, mannitol, starch, dextran, and glucose), proteins (e.g., albumin and casein) or degradation products thereof, protein-containing agents (e.g., bovine serum or skim milk), and buffers (e.g., alkali metal phosphates).

Alternatively, the composition can be formulated as a controlled-release composition. The attenuated/inactivated virus or recombinant vector can be microencapsulated with polymers, such as polycarbonates, polyesters, polyurethanes, polyorthoesters, and polyamides. The particular polymer selected depends on a number of factors including reproducibility of polymer synthesis and microencapsulation, cost of materials and process, toxicological profile, requirements for variable release kinetics, and the physicochemical compatibility of the polymer and the virus/vector.

The compositions described herein can be used alone or in combination with other active ingredients/compositions. Examples include compositions, which can induce an immune response again canine distemper, infectious canine hepatitis (CAV-1 and CAV-2), rabies, parainfluenza, canine corona virus, measles, leptospirosis, and Bordetella. Polyphenols have been disclosed to inhibit influenza infection in humans (see, e.g., U.S. Pat. No. 5,173,922; the '922 patent). Accordingly, the addition of a polyphenol, such as epigallocatechin gallate, epicatechin gallate, epigallocatechin, epicatechin, free theaflavin, theaflavin monogallate A, theaflavin monogallate B, and/or theaflavin digallate may be beneficial (see the '922 patent). Inhibitors of NM are disclosed in U.S. Pat. No. 5,453,533. The use of cytokines as immunopotentiators and liposomal encapsulation are described in U.S. Pat. No. 5,919,480.

The amount of nucleic acid in the composition can vary widely. For example, the concentration can range from less than about 0.1% to as much as about 20-50% or more by weight, usually at least about 2%. The concentration of protein in the composition also can vary widely. For example, the concentration can range from less than about 0.1% to as much as about 20-50% or more by weight, usually at least about 2%. Fluid volume and viscosity are taken into consideration when determining the final concentration.

Accordingly, a method of inducing an immune response to canine influenza virus in an animal is also provided. The susceptibility of an animal to infection can be assessed using the plaque reduction neutralization test (U.S. Pat. No. 4,315,073) or the hemagglutination test. The method comprises administering to the animal an above-described composition comprising an isolated or purified protein/nucleic acid or fragment thereof. If the composition comprises a nucleic acid (or fragment thereof) as part of a vector, preferably the protein (or fragment thereof) is expressed in an amount sufficient to induce an immune response in an animal. For example, a single dose of from about 9 to about 43 international units per kg of animal body weight can be administered. For larger mammals, a single dose can comprise from about 600 to about 3,000 international units per kg of body weight. For vaccine compositions prepared by culturing virus in the allantoic cavity of fertile eggs, harvesting the virus, and, if desired, stabilizing the harvested virus with a stabilizer, such as a peptone or sucrose, and then distribution into glass vials for subsequent freeze-drying, an effective vaccine dosage unit can contain at least $10^7$ EID$_{50}$ (50% egg-infective dose) of virus. In the latter situation, the freeze-dried vaccine is reconstituted by addition of water or another pharmaceutically acceptable diluent prior to administration, such as in the form of a nasal spray or nasal drops. If desired, the vaccine can be administered in two successive dosages at a one-week interval.

The composition can be administered to puppies as a single dose at the age of 12 weeks, or repeatedly starting from the age of 6 weeks (e.g., at 6, 9 and 12 weeks), or weekly from 4 weeks on. The effective dosage and route of administration are determined by the nature of the composition, the nature of the expression product, $LD_{50}$, and, if recombinant vector is used, the expression level of the vector, as well as the breed of dog and its age, sex, weight, and condition. Dosages of expressed product can range from a few to a few hundred micrograms, e.g., 5-500 μg. Preferred dosages of virus or recombinant vector can range from about $10^3$ to about $10^6$ pfu. The dose for the live attenuated strain can be at least about $10^3$ $TCID_{50}$.

The compositions can be administered parenterally (i.e., by injection (e.g., intradermal, subcutaneous, or intramuscular) or by the route of infection, such as nasally) or enterally (i.e., by oral administration). The use of a gelling agent and a muco- or bio-adhesive to enhance the immune response against an intradermally administered immunogenic composition is described in U.S. Pat. App. Pub. No. 2005/0255121. If desired, the composition for inducing an immune response can be administered through drinking water or syrup in accordance with Chu et al. (U.S. Pat. App. Pub. No. 2006/0171960, which was published on Aug. 3, 2006). Oral administration is advantageous inasmuch as it avoids time-consuming and labor-intensive intramuscular injection, which, in turn, can create stress for the animal and discomfort. Discomfort, in turn, can affect the performance of race dogs. Alternatively, the composition comprising a recombinant vector expressing at least one immune response-inducing epitope can be applied directly to the skin for localized expression and induction of an immune response.

Efficacy of the composition, which can induce an immune response, can be demonstrated by exposing puppies to a virulent strain of canine influenza virus. Untreated dogs should develop clinical signs characteristic of canine influenza viral infection, whereas treated dogs should not.

The recombinant vectors and the products expressed from them can be used to produce antibodies, such as polyclonal antibodies (pAb) and monoclonal antibodies (mAb), in accordance with methods known in the art (Harlow and Lane, *Antibodies: A Laboratory Manual*, Cold Spring Harbor Laboratory Press, Cold Spring Harbor, N.Y. (1988); Harlow and Lane, *Using Antibodies: A Laboratory Manual* (1998), Cold Spring Harbor Laboratory Press, Cold Spring Harbor, N.Y. (1998); Shepherd and Dean, *Monoclonal Antibodies: A Practical Approach*, Oxford University Press, U.S.A. (2000)); and Harris and Adair, *Antibody Therapeutics*, CRC Press, Inc., Boca Raton, Fla. (1997)). The antibodies, in particular mAbs, can be used in binding assays and diagnostic kits/tests to determine the presence/absence of an antigen of canine influenza virus or whether or not an immune response to the virus has been stimulated. The antibodies also can be used to recover material by immuno-adsorption chromatography.

Antibodies also can provide passive immunization. For example, partially purified immune sera from host animals or from hybridoma cell lines can be injected into an animal. The antibodies provide a therapeutic effect by binding to and neutralizing an infectious influenza virus.

A composition comprising an anti-idiotypic antibody having an internal image of an epitope of an above-described protein, such as a protein consisting of the amino acid sequence SEQ ID NO: 1 or SEQ ID NO: 3, is also provided.

One of ordinary skill in the art will appreciate that an anti-idiotypic antibody, which bears an internal image of an epitope, such as those described herein, can be prepared. See, e.g., Herlyn et al., Science 232: 100-102 (1986)). Methods of preparing monoclonal and polyclonal anti-idiotypic antibodies, which bear the internal image of the polypeptide, are described in U.S. Pat. No. 5,053,224, for example. Briefly, polyclonal anti-idiotypic antibodies can be produced by immunizing animals with monoclonal idiotypic antibodies raised against the polypeptide and screened for reactivity with the polypeptide and screening for antisera, which react with idiotypic antibodies to the polypeptide. Monoclonal antibodies (mAbs) also can be prepared from such animals using standard techniques of immortalizing the antibody-secreting cells of the animal and screening cultures with idiotypic antibodies in competition with the polypeptide. While mAbs are preferred, polyclonal antibodies (pAbs), which are prepared in a variety of mammalian systems, also can be used.

Another method for inducing an immune response to CIV in a canine is also provided. This method comprises administering to the canine an effective amount of a composition comprising an anti-idiotypic antibody as described above.

The isolated or purified nucleic acid molecules or vectors comprising them can be used to generate DNA for probes/primers, which can be used to detect the presence or absence of hybridizable DNA or to amplify DNA, such as cDNA.

Labeled proteins or fragments thereof, as well as labeled nucleic acids or fragments thereof, can be used in assays. Assay methods include fluoroimmunoassays (smith et al., Ann. Clin. Biochem. 18: 253-275 (1981)), radioimmunoassays (RIA), enzyme-linked immunosorbent assays (ELISA), and enzyme-multiplied immunoassay technique (EMIT; see *Enzyme Immunoassay*, Maggio, ed., CRC Press, Inc., Boca Raton, Fla., 1980. pp. 141-150; 234-235, and 242-243). Such methods can be used to detect the presence of the virus and to diagnose the state of infection.

The virus, itself, can be used as a vector. The use of viruses as vectors is within the skill in the art.

EXAMPLE

The following example serves to illustrate the present invention. The example is not intended to limit the scope of the invention in any way. The example describes the identification and partial characterization of a canine influenza virus.

Outbreaks of acute respiratory disease, characterized by cough, fever, rapid respiration, and hemorrhagic nasal discharge, occurred among greyhounds within two race track compounds located in eastern and western Iowa. in April 2005. While a large percentage of affected dogs recovered, many succumbed to hemorrhagic pneumonia.

Lungs of affected dogs exhibited extensive red to red-black discoloration with moderate to marked palpable firmness and mild fibrinous pleuritis. Lung sections were characterized by severe hemorrhagic interstitial to bronchointerstitial pneumonia. Patchy interstitial change with alveolar septal thickening, coagulums of debris in alveoli, and associated atelectasis were evident. Focally extensive pyogranulomatous bronchointerstitial pneumonia with dilatation of airways by degenerate cells and debris was observed. Scattered vasculitis and vasular thrombi were apparent.

Microbiological testing for conventional viral and bacterial agents did not reveal any significant pathogens except *Streptococcus equi* subsp. *zooepidemicus*, which was present in lung tissues from all animals examined. Two of four lung samples tested positive for influenza virus using real-time reverse transcriptase-polymerase chain reaction (RT-PCR; Harmon et al., Development of a PCR-based differential test for HINI and H3N2 swine influenza viruses. In: *Proceedings of the 42nd Annual Meeting of American Association of Veterinary Laboratory Diagnosticians*. San Diego, Calif. October 1999. p. 44.). Immunohistochemistry using monoclonal antibody (mAb) specific for the NP of influenza virus (Vincent et al., J. Vet. Diagn. Invest. 9: 191-195 (1997)) was also positive within viral pneumonic lesions of both lungs as was antigen-capturing ELISA (Directgen™ Flu A, Becton/Dickinson, Sparks, Md.) testing on the samples. Bronchioalveolar lavage samples from the two positive lungs tested positive for influenza virus by PCR.

Virus isolation was attempted because the detection of influenza virus in canine lungs was an unexpected observation, since only a single report of influenza virus infection in dogs existed (Dubovi et al., Isolation of equine influenza virus from racing greyhounds with fatal hemorrhagic pneumonia. In: *Proceedings of the 47th Annual Meeting of American Association of Veterinary Laboratory Diagnosticians*. Greensboro, N.C. October 2004. p. 158.). A virus that was able to agglutinate rooster red blood cells was isolated in Madin-Darby canine kidney (MDCK) cells from lung and bronchioalveolar lavage fluid of one of the two animals in which influenza virus was detected by immunohistochemical (IHC) assay and PCR. The isolate was determined by PCR to be influenza virus of H3 subtype. The virus isolate was subtyped as H3N8 using HA-inhibition and NM-inhibition assays. The virus isolate was recognized by antisera raised against various H3 equine influenza viruses, including Miami ((A/Eq/MI/1/63-H3N8) 640-1280), AK((A/Eq/AK/29759/91-H3N8) 320-640), and Kentucky ((A/Eq/Kentucky/81-H3N8) 160-320).

Sequencing of HA and NA genes of both isolates revealed 100% and 99.8% identity, respectively, between the two isolates. Phylogenetically, the HA gene of the isolates was genetically close (96-98% nucleotide homology) to the HA gene of recent H3N8 equine influenza viruses (Macken et al., The value of a database in surveillance and vaccine selection. In: *Options for the Control of Influenza IV*. Osterhaus et al., eds. Elsevier Science, Amsterdam. 2001. pp. 103-106.). The NA gene of the isolates also showed 96-98% homology with the NA gene of recent H3N8 equine influenza viruses. Since greyhounds in two different race tracks, which are geographically remote in Iowa, simultaneously succumbed to the disease without the involvement of sick horses indicates that the influenza virus isolate is a canine-adapted strain that can perpetuate in and spread among dogs. *S. zooepidemicus*, which has been implicated in respiratory disease and septicemia-associated problems in many different animal species (Wood et al., J. Clin. Microbiol. 43: 120-126 (2005); and Gillespie et al., The General Staphylococcus and Streptococcus. In: *Hagan and Bruner's Infectious Diseases of Domestic Animals*. 7th ed. Comstock/Cornell University Press. Ithaca, N.Y. 1981. pp. 164-180)), probably contributed to the severity of the disease.

All references, including publications, patent applications, and patents, cited herein are hereby incorporated by reference to the same extent as if each reference were individually and specifically indicated to be incorporated by reference and were set forth in its entirety herein.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate better the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. An isolated canine influenza virus of subtype H3N8 comprising a hemagglutinin (HA) having SEQ ID NO: 4 or an amino acid sequence that is greater than 99% identical to SEQ ID NO: 4, with the proviso that the amino acids at positions 94 and 233 are identical to SEQ ID NO: 4.

2. The isolated canine influenza virus of claim 1, which comprises a neuraminidase (NA) comprising the amino acid sequence of SEQ ID NO: 2 or an amino acid sequence that is greater than 99% identical to SEQ ID NO: 2, with the proviso that the amino acids at positions 68 and 134 are identical to SEQ ID NO: 2.

3. The isolated canine influenza virus of claim 2, which further comprises at least one of the following: a nucleoprotein (NP) having the amino acid sequence of SEQ ID NO: 6 or an amino acid sequence that is greater than 99% identical to SEQ ID NO: 6, with the proviso that amino acid 402 is identical to that of SEQ ID NO: 6; a matrix 1 protein (M1)

having the amino acid sequence of SEQ ID NO: 8 or an amino acid sequence that is greater than 99% identical to SEQ ID NO: 8, with the proviso that amino acid 111 is identical to that of SEQ ID NO: 8; a nonstructural protein 1 (NS1) having the amino acid sequence of SEQ ID NO: 10; a PA protein having the amino acid sequence of SEQ ID NO: 12 or an amino acid sequence that is greater than 98% identical to SEQ ID NO: 12, with the proviso that amino acids 233, 256, 327, and 561 are identical to SEQ ID NO: 12; a PB1 having the amino acid sequence of SEQ ID NO: 14 or an amino acid sequence that is greater than 99% identical to SEQ ID NO: 14, with the proviso that amino acids 200 and 213 are identical to SEQ ID NO: 14; and/or PB2 having the amino acid sequence of SEQ ID NO: 16 or an amino acid sequence that is greater than 99% identical to SEQ ID NO: 16, with the proviso that amino acids 107, 221, 292, and 661 are identical to SEQ ID NO: 16.

4. The isolated canine influenza virus of claim 1, which is attenuated.

5. A composition comprising the isolated canine influenza virus of claim 4 in an amount sufficient to induce an immune response.

6. The isolated canine influenza virus of claim 1, which is inactivated.

* * * * *

UNITED STATES PATENT AND TRADEMARK OFFICE
CERTIFICATE OF CORRECTION

| | | |
|---|---|---|
| PATENT NO. | : 7,468,187 B2 | |
| APPLICATION NO. | : 11/539123 | |
| DATED | : December 23, 2008 | |
| INVENTOR(S) | : Yoon et al. | |

It is certified that error appears in the above-identified patent and that said Letters Patent is hereby corrected as shown below:

In Column 72, beginning at line 12, insert claims 7-8 as patented claims after claim 6 as follows:

-- 7. A composition comprising the isolated canine influenza virus of claim 6 in an amount sufficient to induce an immune response. --

-- 8. An isolated canine influenza virus of subtype H3N8 deposited with the American Type Culture Collection as Patent Deposit No. PTA-7694. --

Signed and Sealed this
Twenty-first Day of February, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,468,187 B2 | |
| APPLICATION NO. | : 11/539123 | |
| DATED | : December 23, 2008 | |
| INVENTOR(S) | : Yoon et al. | |

It is certified that error appears in the above-identified patent and that said Letters Patent is hereby corrected as shown below:

Delete the title page and substitute therefore the attached title page showing the corrected number of claims in patent.

In Column 72, beginning at line 12, insert claims 7-8 as patented claims after claim 6 as follows:

-- 7. A composition comprising the isolated canine influenza virus of claim 6 in an amount sufficient to induce an immune response. --

-- 8. An isolated canine influenza virus of subtype H3N8 deposited with the American Type Culture Collection as Patent Deposit No. PTA-7694. --

This certificate supersedes the Certificate of Correction issued February 21, 2012.

Signed and Sealed this
Twentieth Day of March, 2012

David J. Kappos
*Director of the United States Patent and Trademark Office*

(12) United States Patent
Yoon et al.

(10) Patent No.: US 7,468,187 B2
(45) Date of Patent: Dec. 23, 2008

(54) CANINE INFLUENZA VIRUS AND RELATED COMPOSITIONS AND METHODS OF USE

(75) Inventors: Kyoung-Jin Yoon, Ames, IA (US); Vickie Cooper, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 11/539,123

(22) Filed: Oct. 5, 2006

(65) Prior Publication Data
US 2007/0098742 A1 May 3, 2007

Related U.S. Application Data

(60) Provisional application No. 60/727,808, filed on Oct. 18, 2005.

(51) Int. Cl.
*A61K 39/145* (2006.01)
*A61K 39/00* (2006.01)
*A61K 39/12* (2006.01)
*A61K 39/02* (2006.01)

(52) U.S. Cl. ............... 424/209.1; 424/185.1; 424/186.1; 424/204.1

(58) Field of Classification Search .................. None
See application file for complete search history.

(56) References Cited

U.S. PATENT DOCUMENTS

| | | |
|---|---|---|
| 3,991,179 A | 11/1976 | Beare et al. |
| 4,009,258 A | 2/1977 | Kilbourne |
| 4,029,763 A | 6/1977 | Kilbourne |
| 4,140,762 A | 2/1979 | Bachmayer et al. |
| 4,278,662 A | 7/1981 | Löbmann et al. |
| 4,318,903 A | 3/1982 | Löbmann et al. |
| 4,338,296 A | 7/1982 | Löbmann et al. |
| 4,693,893 A | 9/1987 | Campbell |
| 4,826,687 A | 5/1989 | Nerome et al. |
| 5,136,019 A | 8/1992 | Judd et al. |
| 5,162,112 A | 11/1992 | Oxford et al. |
| 5,616,327 A | 4/1997 | Judd et al. |
| 5,741,493 A | 4/1998 | Moste-Deshairs et al. |
| 5,762,939 A | 6/1998 | Smith et al. |
| 6,245,532 B1 | 6/2001 | Smith et al. |
| 6,605,457 B1 | 8/2003 | Fiers et al. |
| 6,740,325 B1 | 5/2004 | Arnon et al. |
| 2003/0129197 A1 | 7/2003 | Fiers et al. |
| 2003/0199074 A1 | 10/2003 | Dowling et al. |
| 2007/0082012 A1* | 4/2007 | Shields et al. ........... 424/209.1 |

FOREIGN PATENT DOCUMENTS

| | | |
|---|---|---|
| WO | WO 00/09702 | 8/2000 |
| WO | WO 01/60849 | 2/2001 |

OTHER PUBLICATIONS

Anderson et al., "Canine Influenza Virus Agglutination of Avian and Mammalian Red Blood Cells," *Proceedings of the American Association of Veterinary Laboratory Diagnosticians 49th Annual Conference*, p. 44 (2006).

Anderson et al., "Development of a Hemagglutination Inhibition Assay for Diagnosis of Canine Influenza Virus Infection," *Proceedings of the American Association of Veterinary Laboratory Diagnosticians 49th Annual Conference*, p. 45 (2006).

Crawford et al., "Transmission of Equine Influenza Virus to Dogs," *Science*, 310: pp. 482-485 (2005).

Daly, "Equine Influenza in dogs: Too late to bolt the stable door?," *The Veterinary Journal*, 171 pp. 7-8 (2006).

Dubovi et al., "Isolation of Equine Influenza Virus from Racing Greyhounds with Fatal Hemorrhagic Pneumonia," In: *Proceedings of the 47th Annual Meeting of American Association of Veterinary Laboratory Diagnosticians*, Greensboro, NC. p. 158 (2005).

Joly, "Canine Influenza Virus" *The Veterinary Record*, p. 527 (2005).

Keawcharoen et al., "Avian Influenza H5N1 in Tigers and Leopards," *Emerg. Infect. Dis.*, 10: pp. 2189-2191 (2004).

Macken et al., "The value of a database in surveillance and vaccine selection," In: *Options for the Control of Influenza IV*, Osterhaus et al., eds. Elsevier Science, Amsterdam, pp. 103-106 (2001).

Smith et al., "Canine Influenza Virus" *The Veterinary Record*, p. 599 (2005).

Yoon et al., "Influenza Virus Infection in Racing Greyhounds," *Emerg. Infect. Dis.*, 11(12): pp. 1974-1976 (2005).

Crawford et al.: "Influenza A virus (A/canine/Texas/1/2004 (H3N9))" Database accession No. DQ124159 (2005).

Quinlivan et al., "Attenuation of equine influenza viruses through truncations of the N protein," Database accession No. Q5BUA9 (2005).

Quinlivan et al., "Attenuation of equine influenza viruses through truncations of the N protein," Database accession No. Q5BUA7 (2005).

Quinlivan et al ; "Attenuation of equine influenza viruses through truncations of the N protein," Database accession No. Q5BUB2 (2005).

Quinlivan et al.: "Attenuation of equine influenza viruses through truncations of the N protein," Database accession No. Q5BUB3 (2005).

Lindstrom et al.: "Phylogenetic analyses of the matrix and non-structural genes of equine influenza virusesr," Archives of Virology, New York, vol. 143, No. 8, 1998, pp. 1585-1598, NY, US, ISSN: 0304-8608, the whole document (1998).

(Continued)

*Primary Examiner*—Bruce Campell
*Assistant Examiner*—Benjamin P Blumel
(74) *Attorney, Agent, or Firm*—Barnes & Thornburg LLP; Sendil K. Devadas

(57) ABSTRACT

The present invention provides an isolated canine influenza virus of subtype H3N8 comprising an HA having SEQ ID NO: 4 or an amino acid sequence that is greater than 99% identical to SEQ ID NO: 4, with the proviso that the amino acids at positions 94 and 233 are identical to SEQ ID NO: 4; a composition comprising attenuated or inactivated virus; isolated or purified HA, NM, NP, M1, NS1, PA, PB1, and PB2 proteins and fragments thereof and compositions comprising same or nucleic acids, optionally as part of a vector, encoding same; and a method of inducing an immune response to canine influenza virus in an animal comprising administering to the animal an aforementioned composition.

8 Claims, 14 Drawing Sheets